(12) United States Patent
Letzt et al.

(10) Patent No.: US 11,488,492 B2
(45) Date of Patent: Nov. 1, 2022

(54) ADAPTIVE, INTEGRATED, AND INTERACTIVE EDUCATION AND COMMUNICATION SYSTEM FOR PEOPLE WITH HEARING LOSS AND HEARING HEALTHCARE PROVIDERS AND RELATED METHODS

(71) Applicant: Healthcare Technologies and Methods, LLC, Fredericksburg, VA (US)

(72) Inventors: Alan Letzt, Purcellville, VA (US); Stephanie Letzt, Purcellville, VA (US)

(73) Assignee: Healthcare Technologies and Methods, LLC, Fredericksburg, VA (US)

( * ) Notice: Subject to any disclaimer, the term of this patent is extended or adjusted under 35 U.S.C. 154(b) by 0 days.

(21) Appl. No.: 17/501,375

(22) Filed: Oct. 14, 2021

(65) Prior Publication Data

US 2022/0058980 A1 Feb. 24, 2022

Related U.S. Application Data

(63) Continuation of application No. 16/625,196, filed as application No. PCT/US2018/038820 on Jun. 21, 2018, now Pat. No. 11,151,896.

(Continued)

(51) Int. Cl.
*G09B 19/00* (2006.01)
*G16H 40/67* (2018.01)
(Continued)

(52) U.S. Cl.
CPC .............. *G09B 19/00* (2013.01); *A61B 5/123* (2013.01); *A61B 5/4833* (2013.01); *G09B 7/00* (2013.01);
(Continued)

(58) Field of Classification Search
CPC .............................. G09B 19/00; G09B 21/009
(Continued)

(56) References Cited

U.S. PATENT DOCUMENTS 5,434,611 A 7/1995 Tamura
5,867,821 A 2/1999 Ballantyne et al.
(Continued)

FOREIGN PATENT DOCUMENTS

EP 2924676 A1 9/2015

OTHER PUBLICATIONS

Supplementary European Search Report in corresponding European Patent Application No. EP18820690, dated Feb. 1, 2021 (8 pages).

*Primary Examiner* — Thomas J Hong
(74) *Attorney, Agent, or Firm* — Muir Patent Law, PLLC

(57) ABSTRACT

A system, device, and wireless computer technology-implemented method for providing hearing healthcare education and communication for a patient, his/her communication partner, and a hearing care provider. The system provides the patient at least one educational and experiential module and a method for assessing the patient's comprehension of the module's lessons. The system further provides the patient with a method to select personal hearing aid and communication goals; a method to evaluate his/her progress on achieving each personal goal; and a method to report his/her hearing experiences. The system further provides a method to compare data reported by the patient to personalized thresholds. When one or more of the patient's reports do not meet the thresholds, the system sends automated alerts to the hearing care provider to encourage prompt remedial action and sends automated reminders to the patient to improve the patient's ability to achieve his/her personal goals.

15 Claims, 8 Drawing Sheets

Related U.S. Application Data

(60) Provisional application No. 62/640,152, filed on Mar. 8, 2018, provisional application No. 62/522,920, filed on Jun. 21, 2017.

(51) Int. Cl.
  *G16H 20/00*   (2018.01)
  *A61B 5/12*   (2006.01)
  *A61B 5/00*   (2006.01)
  *G09B 7/00*   (2006.01)
  *H04R 25/00*   (2006.01)

(52) U.S. Cl.
  CPC ............ *G16H 20/00* (2018.01); *G16H 40/67* (2018.01); *H04R 25/70* (2013.01); *H04R 2225/55* (2013.01)

(58) Field of Classification Search
  USPC ........................................................ 434/262
  See application file for complete search history.

(56) References Cited

U.S. PATENT DOCUMENTS

| | | |
|---|---|---|
| 5,961,446 A | 10/1999 | Beller et al. |
| 7,185,282 B1 | 2/2007 | Naidoo et al. |
| 7,835,926 B1 | 11/2010 | Naidoo et al. |
| 9,883,240 B2 | 1/2018 | Wessel |
| 2008/0077431 A1 | 3/2008 | Calder et al. |
| 2010/0104122 A1 | 4/2010 | Waldmann |
| 2010/0150384 A1 | 6/2010 | Waldmann |
| 2011/0313315 A1 | 12/2011 | Attias et al. |
| 2012/0077173 A1* | 3/2012 | Crawford ............... G09B 19/06 434/322 |
| 2014/0178846 A1 | 6/2014 | Letzt et al. |
| 2014/0194774 A1 | 6/2014 | Gilligan |
| 2015/0178456 A1 | 6/2015 | Stransky-Heilkron et al. |
| 2015/0208956 A1 | 7/2015 | Schmitt |
| 2016/0066107 A1* | 3/2016 | Recker ................. H04R 25/505 463/31 |
| 2016/0135719 A1 | 5/2016 | Von Kraus et al. |
| 2017/0195739 A1 | 7/2017 | Wessel |

* cited by examiner

ADAPTIVE, INTEGRATED, AND INTERACTIVE EDUCATION AND COMMUNICATION SYSTEM FOR PEOPLE WITH HEARING LOSS AND HEARING HEALTHCARE PROVIDERS AND RELATED METHODS

CROSS-REFERENCE TO RELATED APPLICATIONS

This application is a continuation of U.S. patent application Ser. No. 16/625,196, filed Dec. 20, 2019, which is a U.S. national phase under § 371 of International Patent Application No. PCT/US2018/038820, filed Jun. 21, 2018, which claims the benefit of priority of U.S. Provisional Patent Application No. 62/640,152, filed Mar. 8, 2018, and U.S. Provisional Patent Application No. 62/522,920, filed Jun. 21, 2017, in the United States Patent and Trademark Office, the entire contents of all of which are incorporated herein by reference.

TECHNICAL FIELD

The present disclosure relates to systems, devices, and methods for education and communication for people with hearing loss and, more particularly, to systems, devices, and methods for adaptive and interactive education of people with hearing loss and communication between these people and their hearing healthcare professionals.

BACKGROUND

Hearing loss is reported in 36 million Americans, including 30% of people age 65-74, and 47% of people age 75 or older; however, only 1 in 5 people who could benefit from a hearing aid actually uses one. Hearing loss, when left untreated in older adults, leads to an increased incidence of dementia, risk of falls, social isolation and depression, and reduced quality of life. Further, self-efficacy in hearing aid management is considered to be a major determinant of positive outcomes with older adults. There is a compelling need for innovative approaches designed for use by older adults—starting with patients newly fitted for hearing aids. The major causes of suboptimal hearing aid use include low patient satisfaction and inadequate patient education and follow-up during the fitting and trial period. Also, patients with low health literacy experience reduced recall of information, poor hearing aid use and maintenance, unrealistic expectations, and difficulties articulating their needs to audiologists. Limited mobility and transportation access further reduce older patients' follow-up visits with their audiologists. A novel approach to hearing aid education and communication may better meet the needs of older adults with hearing loss and better connect them with their audiologists for aftercare.

Many older adults who are dealing with hearing loss are at a disadvantage because audiologists have limited available time to: (a) educate them about their hearing aids, (b) train them on critical communications strategies needed to supplement their hearing aids, and (c) provide hearing aid aftercare for their patients. Hearing aid aftercare includes answering patients' questions about hearing aid use and maintenance and follow-on office visits to troubleshoot hearing aid problems and learn adaptive communications skills. Furthermore, many of such individuals either do not use computers or have low computer proficiency, and because they also have low health literacy they cannot benefit from many of the resources on conventional Internet websites. As a result of these conditions, more than 20% of people who purchase hearing aids get frustrated and return them while an equally high percentage simply leave them in a drawer, unused. Both of these outcomes result in older patients resigning themselves to a life with an unaided hearing deficit, which, according to the literature, often results in social isolation, depression and higher susceptibility to chronic illnesses such as diabetes and dementia.

Currently, traditional hearing aid instruction manuals are unsuitable for the majority of hearing aid users in terms of language level, jargon, and design. Educational DVDs, while offering good content, are neither individualized nor interactive, and have met with limited success as fewer than 30% of patients actually watch them. Also, limited Internet-based education is available. However, these websites do not link patients to their audiologists and most do not adequately address health literacy and other issues critical to older adult learning such as suitable fonts, colors and contrast. What is needed to keep a higher percentage of older adults successfully using their hearing aids, rather than returning them or placing them in a drawer, is a patient-centered and interactive system that links patients to their hearing care professionals (HCPs) and allows older adults to easily access and use the system on familiar technology in the convenience of their home. The standard home TV is such a familiar technology. It is also a valued medium because is large screen and better speakers facilitate the hearing aid education of the primary communication partners of the adult with hearing loss. In this novel and easy-to-use system, an integrated combination of personalized educational reinforcement, reminders, reports and alerts will improve patient-HCP communications and will facilitate more timely remedial hearing aid-related interventions.

SUMMARY

In accordance with aspects of the present disclosure, the present disclosure is directed to a method for providing hearing healthcare education and communication, the method comprising: providing, to the patient, a set of education goals related to the hearing aid; receiving, from the patient, input data defining a subset of the set of the education goals; storing the subset of the set of the education goals as personal goals of the patient; providing, to the patient, at least one educational and experiential module related to the personal goals; determining a hearing aid achievement of the patient, the hearing aid achievement corresponding to a use of the at least one educational and experiential module by the patient and a level of compliance with the personal goals by the patient; based on the hearing aid achievement, automatically providing at least one of a message or an alert to bring the patient into compliance with the personal goals; and providing a recommended adjustment to the hearing aid based on the hearing aid achievement.

In some aspects, the method further includes wherein the at least one educational and experiential module includes content review questions, and wherein the determining the hearing aid achievement of the patient includes: providing, to the patient, at least one content review question about content of the at least one educational and experiential module; receiving, from the patient, a patient response to the at least one content review question; comparing the patient response to a correct response; determining if the patient response is the correct response; determining a content review score based on a percentage of correct responses; and based on a result of the determining the content review score, determining whether to automatically send the at least one of the message to the patient and the alert to a hearing healthcare provider.

In some aspects, the method further includes wherein the determining the hearing aid achievement of the patient further includes: collecting patient viewing data related to the at least one educational and experiential module; comparing the patient viewing data to a corresponding threshold value; based on a result of the comparing, determining how the patient viewing data corresponds to the corresponding threshold value; and based on the result of the determining, determining whether to send the at least one of the message to the patient and the alert to a hearing healthcare provider.

In some aspects, the method further includes at least one of: providing one or more patient reports, wherein the one or more patient reports include a patient presentation of the patient viewing data and a content review score; and providing one or more provider reports, wherein the one or more provider reports include a provider presentation of the patient viewing data and the content review score.

In some aspects, the method further includes wherein the at least one educational and experiential module is an educational video, and wherein the patient viewing data includes a cumulative number of different videos viewed within a predetermined period of time.

In some aspects, the method further includes wherein the determining the hearing aid achievement of the patient further includes: providing, to the patient, a survey question about a hearing aid experience of the patient; and receiving, from the patient, a patient response to the survey question; comparing the patient response to a threshold value; determining how the patient response compares to the threshold value; and based on a result of the determining, determining whether to send the at least one of the message to the patient and the alert to a hearing healthcare provider.

In some aspects, the method further includes collecting system usage data of a hearing healthcare education and communication system, the system usage data measuring usage of the hearing healthcare education and communication system by the patient and usage of at least one specific feature of the hearing healthcare education and communication system; comparing the system usage data to a threshold value; determining how the system usage data compares to the threshold value; storing the system usage data and a result of the comparing; and based on the result of the determining, determining whether to send the at least one of the message to the patient and the alert to a hearing healthcare provider.

In some aspects, the method further includes at least one of: providing one or more patient reports, wherein the one or more patient reports include a patient presentation of the system usage data; and providing one or more provider reports, wherein the one or more provider reports include a provider presentation of the system usage data.

In some aspects, the method further includes wherein the system usage data includes at least one of: a number of times that features of the hearing healthcare education and communication system are accessed by the patient, a number of specific features of the hearing healthcare education and communication system that are used by the patient, and a number of specific features of the hearing healthcare education and communication system used by the patient within a predetermined period of time.

In some aspects, the method further includes wherein the at least one educational and experiential module includes troubleshooting information related to a hearing aid problem, and the method further includes: providing, to the patient, troubleshooting questions related to patient experiences using the hearing aid; receiving, from the patient, patient responses to the troubleshooting questions; providing troubleshooting advice based on the patient responses to the troubleshooting questions; and storing troubleshooting result data based on the patient responses to the troubleshooting questions and success of the patient in resolving the hearing aid problem.

In some aspects, the method further includes at least one of: providing one or more patient reports based on the troubleshooting result data, wherein the one or more patient reports include a presentation of the troubleshooting result data; and providing one or more provider reports based on the troubleshooting result data, wherein the one or more provider reports include a presentation of the troubleshooting result data.

In some aspects, the method further includes wherein the providing the one or more provider reports includes: providing the alert to a hearing healthcare provider to notify the hearing healthcare provider that the patient has one or more problems with the hearing aid.

In some aspects, the method further includes wherein the troubleshooting advice may include automatically presenting at least one education video to the patient.

In accordance with aspects of the present disclosure, the present disclosure is directed to a system for providing hearing healthcare education and communication, comprising: at least one storage device storing instructions; and at least one computer processor configured to execute the instructions and to cause the system to perform operations comprising: providing, to the patient, a set of education goals related to the hearing aid; receiving, from the patient, input data defining a subset of the set of the education goals as personal goals of the patient; storing, in the at least one storage device, the subset of the set of the education goals as the personal goals of the patient; providing, to the patient, at least one educational and experiential module related to the personal goals; determining a hearing aid achievement of the patient, the hearing aid achievement corresponding to a use of the at least one educational and experiential module by the patient and a level of compliance with the personal goals by the patient; based on the hearing aid achievement, automatically providing at least one of a message or an alert to bring the patient into compliance with the personal goals; and providing a recommended adjustment to the hearing aid based on the hearing aid achievement.

In some aspects, the system further includes wherein the at least one educational and experiential module includes content review questions, and wherein the determining the hearing aid achievement of the patient further includes: providing, to the patient, at least one content review question about content of the at least one educational and experiential module; receiving, from the patient, a patient response to the at least one content review question; comparing the patient response to a correct response; determining if the patient response is the correct response; determining a content review score based on a percentage of correct responses; and based on a result of the determining the content review score, determining whether to automatically send the at least one of the message to the patient and the alert to a hearing healthcare provider.

In some aspects, the system further includes wherein the determining the hearing aid achievement of the patient includes: collecting patient viewing data related to the at least one educational and experiential module; comparing the patient viewing data to a threshold value; based on a result of the comparing, determining how the patient viewing data corresponds to the threshold value; and based on the result of the determining, determining whether to automatically send the at least one of the message to the patient and the alert to a hearing healthcare provider.

In some aspects, the system further includes wherein the at least one computer processor is further configured to execute the instructions and to cause the system to perform operations comprising at least one of: providing one or more patient reports, wherein the one or more patient reports include a patient presentation of the patient viewing data and a content review score; and providing one or more provider reports, wherein the one or more provider reports include a provider presentation of the patient viewing data and the content review score.

In some aspects, the system further includes wherein the at least one educational and experiential module is an educational video, and wherein the patient viewing data includes a cumulative number of different videos viewed within a predetermined period of time.

In some aspects, the system further includes wherein the determining the hearing aid achievement of the patient further includes: providing, to the patient, a survey question about a hearing aid experience of the patient; and receiving, from the patient, a patient response to the survey question; comparing the patient response to a threshold value; determining how the patient response compares to the threshold value; and based on a result of the determining, determining whether to automatically send the at least one of the message to the patient and the alert to a hearing healthcare provider.

In some aspects, the system further includes wherein the at least one computer processor is further configured to execute the instructions and to cause the system to perform operations comprising: collecting system usage data of the system, the system usage data measuring usage of the system by the patient and usage of at least one specific feature of the system; comparing the system usage data to a threshold value; determining how the system usage data compares to the threshold value; storing the system usage data and a result of the comparing in the at least one storage device; and based on the result of the determining, determining whether to send the at least one of the message to the patient and the alert to a hearing healthcare provider.

In some aspects, the system further includes wherein the at least one computer processor is further configured to execute the instructions and to cause the system to perform operations comprising at least one of: providing one or more patient reports, wherein the one or more patient reports include a patient presentation of the system usage data; and providing one or more provider reports, wherein the one or more provider reports include a provider presentation of the system usage data.

In some aspects, the system further includes wherein the system usage data includes at least one of: a number of times that features of the system are accessed by the patient, a number of specific features of the system that are used by the patient, and a number of specific features of the system used by the patient within a predetermined period of time.

In some aspects, the system further includes wherein the at least one educational and experiential module includes troubleshooting information related to a hearing aid problem, and the at least one computer processor is further configured to execute the instructions and to cause the system to perform operations comprising: providing, to the patient, troubleshooting questions related to patient experiences using the hearing aid; receiving, from the patient, patient responses to the troubleshooting questions; providing troubleshooting advice based on the patient responses to the troubleshooting questions; and storing, in the at least one storage device, troubleshooting result data based on the patient responses to the troubleshooting questions and a success of the patient in resolving the hearing aid problem.

In some aspects, the system further includes wherein the at least one computer processor is further configured to execute the instructions and to cause the system to perform operations comprising at least one of: providing one or more patient reports based on the troubleshooting result data, wherein the one or more patient reports include a presentation of the troubleshooting result data; and providing one or more provider reports based on the troubleshooting result data, wherein the one or more provider reports include a presentation of the troubleshooting result data.

In some aspects, the system further includes wherein the providing the one or more provider reports includes: providing the alert to a hearing healthcare provider to notify the hearing healthcare provider that the patient has one or more problems with the hearing aid.

In some aspects, the system further includes wherein the troubleshooting advice may include automatically presenting at least one education video to the patient.

In accordance with aspects of the present disclosure, the present disclosure is directed to a method for providing hearing healthcare education and communication, the method comprising: receiving, via a hearing healthcare provider computing device, initial patient data, the initial patient data including one or more values identifying an individual patient and a hearing aid used by the individual patient; receiving, via the hearing healthcare provider computing device, individualized healthcare rules from a hearing healthcare provider, each of the individualized healthcare rules being defined for the individual patient; providing, via a patient computing device, a request for input patient data related to the individual patient based on the individualized healthcare rules; transmitting the request for the input patient data to a display device for display; providing on the patient computing device a remote control interface that allows the individual patient to navigate the hearing healthcare education and communication system and respond to the request for the input patient data; receiving the input patient data in response to the request displayed on the display device by using the remote control interface on the patient computing device; storing the input patient data; for each of the individualized healthcare rules: comparing the input patient data to the corresponding individualized healthcare rule to determine a threshold comparison decision defined by the individualized healthcare rule; and based on the threshold comparison decision, automatically providing at least one of a message or an alert to bring the individual patient into compliance with the individualized healthcare rule, wherein the individualized healthcare rules include one or more of patient system usage rules, patient education rules, and patient hearing aid experience rules.

In some aspects, the method further includes wherein the comparing the input patient data to the individualized healthcare rule to determine the threshold comparison decision further includes: comparing the input patient data to a threshold value of the individualized healthcare rule to determine if the input patient data is equal to or greater than the threshold value; storing a result of the comparing as result data; and when the input patient data is not determined to be equal to or greater than the threshold value, transmitting the alert to the hearing healthcare provider computing device and the message to a hearing healthcare provider mobile device.

In some aspects, the method further includes wherein the comparing the input patient data to the individualized healthcare rule to determine the threshold comparison decision further includes: comparing the input patient data to a threshold value of the individualized healthcare rule to determine if the input patient data is equal to or greater than the threshold value; storing a result of the comparing as result data; and when the input patient data is determined to be equal to or greater than the threshold value, transmitting the alert to the hearing healthcare provider computing device and the message to a hearing healthcare provider mobile device.

In some aspects, the method further includes providing, to the patient computing device, an educational and experiential module based on the individualized healthcare rules received from the hearing healthcare provider; and displaying the educational and experiential module on the display device, wherein the educational and experiential module includes an educational video and the input patient data includes responses to questions about a content of the education video.

In some aspects, the method further includes providing, to the patient computing device, an educational and experiential module based on the individualized healthcare rules received from the hearing healthcare provider; and displaying the educational and experiential module on the display device, wherein the educational and experiential module includes a request for patient input regarding the hearing aid and the input patient data includes responses related to an amount of time the individual patient wears the hearing aid, a perceived comfort level of the individual patient while wearing the hearing aid, and a perceived sound quality level of the individual patient while wearing the hearing aid.

In some aspects, the method further includes wherein the input patient data includes responses related to at least one of a hearing aid wear time value reflecting an amount of time the individual patient wears the hearing aid, a hearing aid comfort value reflecting a perceived comfort level of the individual patient while wearing the hearing aid, and a sound quality value reflecting a perceived sound quality level of the individual patient while wearing the hearing aid, and wherein the individualized healthcare rules comprise threshold values related to the hearing aid, the threshold values including at least one of a hearing aid wear time threshold value, a hearing aid comfort threshold value, and a sound quality threshold value.

In some aspects, the method further includes wherein the comparing the input patient data to the individualized healthcare rules includes at least one of: comparing the hearing aid wear time value with the hearing aid wear time threshold value, comparing the hearing aid comfort value with the hearing aid comfort threshold value, and comparing the sound quality value with the sound quality threshold value.

In some aspects, the method further includes storing initial patient data in a database; storing the individualized healthcare rules in the database; and generating a correspondence between the initial patient data and the individualized healthcare rules.

In some aspects, the method further includes collecting system usage data of a hearing healthcare education and communication system, the system usage data measuring usage of the hearing healthcare education and communication system by the patient and usage of at least one specific feature of the hearing healthcare education and communication system; comparing the system usage data to a corresponding set of threshold values; determining how the system usage data compares to the corresponding set of threshold values; storing the system usage data and a result of the comparing; and based on the result of the determining, determining whether to send the at least one of the message to the patient and the alert to the hearing healthcare provider.

In some aspects, the method further includes at least one of: providing, via the patient computing device, one or more patient reports, wherein the one or more patient reports include a patient presentation of the system usage data; and providing, via the provider computing device, one or more provider reports, wherein the one or more provider reports include a provider presentation of the system usage data.

In some aspects, the method further includes wherein the system usage data includes at least one of: a number of times that features of the hearing healthcare education and communication system are accessed via the patient computing device, a number of specific features of the hearing healthcare education and communication system that are accessed via the patient computing device, and a number of specific features of the hearing healthcare education and communication system that are accessed via the patient computing device within a predetermined period of time.

In accordance with aspects of the present disclosure, the present disclosure is directed to a system for providing hearing healthcare education and communication, comprising: at least one storage device storing instructions; and at least one computer processor configured to execute the instructions and to cause the system to perform operations comprising: receiving, via a hearing healthcare provider computing device, initial patient data, the initial patient data including one or more values identifying an individual patient and a hearing aid used by the individual patient; receiving, via the hearing healthcare provider computing device, individualized healthcare rules from a hearing healthcare provider, each of the individualized healthcare rules being defined for the individual patient; providing, via a patient computing device, a request for input patient data related to the individual patient based on the individualized healthcare rules; transmitting the request for the input patient data to a display device for display; providing on the patient computing device a remote control interface that allows a patient to navigate system and respond to the request for the input patient data; receiving the input patient data in response to the request displayed on the display device by using the remote control interface; storing the input patient data in the at least one storage device; for each of the individualized healthcare rules: comparing the input patient data to the corresponding individualized healthcare rule to determine a threshold comparison decision defined by the individualized healthcare rule; and based on the threshold comparison decision, automatically providing at least one of a message or an alert to bring the individual patient into compliance with the individualized healthcare rule, wherein the individualized healthcare rules include one or more of patient system usage rules, patient education rules, and patient hearing aid experience rules.

In some aspects, the system further includes wherein the comparing the input patient data to the individualized healthcare rule to determine the threshold comparison decision further includes: comparing the input patient data to a threshold value of the individualized healthcare rule to determine if the input patient data is equal to or greater than the threshold value; storing a result of the comparing as result data in the at least one storage device; and when the input patient data is determined not to be equal to or greater than the threshold value, transmitting the alert to the hearing healthcare provider computing device and the message to a hearing healthcare provider mobile device.

In some aspects, the system further includes wherein the comparing the input patient data to the individualized healthcare rule to determine the threshold comparison decision further includes: comparing the input patient data to a threshold value of the individualized healthcare rule to determine if the input patient data is equal to or greater than the threshold value; storing a result of the comparing as result data in the at least one storage device; and when the input patient data is determined to be equal to or greater than the threshold value, transmitting the alert to the hearing healthcare provider computing device and the message to a hearing healthcare provider mobile device.

In some aspects, the system further includes wherein the at least one computer processor is further configured to execute the instructions and to cause the system to perform operations comprising: providing, to the patient computing device, an educational and experiential module based on the individualized healthcare rules received from the hearing healthcare provider; and displaying the educational and experiential module on the display device, wherein the educational and experiential module include an educational video and the input patient data includes responses to questions about a content of the education video.

In some aspects, the system further includes wherein the at least one computer processor is further configured to execute the instructions and to cause the system to perform operations comprising: providing, to the patient computing device, an educational and experiential module based on the individualized healthcare rules received from the hearing healthcare provider computing device; and displaying the educational and experiential module on the display device, wherein the educational and experiential module includes a request for patient input regarding the hearing aid and the input patient data includes responses related to an amount of time the individual patient wears the hearing aid, a perceived comfort level of the individual patient while wearing the hearing aid, and a perceived sound quality level of the individual patient while wearing the hearing aid.

In some aspects, the system further includes wherein the input patient data includes responses related to at least one of a hearing aid wear time value reflecting an amount of time the individual patient wears the hearing aid, a hearing aid comfort value reflecting a perceived comfort level of the individual patient while wearing the hearing aid, and a sound quality value reflecting a perceived sound quality level of the individual patient while wearing the hearing aid, and wherein the individualized healthcare rules comprise threshold values related to the hearing aid, the threshold values including at least one of a hearing aid wear time threshold value, a hearing aid comfort threshold value, and a sound quality threshold value.

In some aspects, the system further includes wherein the comparing the input patient data to the individualized healthcare rules includes at least one of: comparing the hearing aid wear time value with the hearing aid wear time threshold value, comparing the hearing aid comfort value with the hearing aid comfort threshold value, and comparing the sound quality value with the sound quality threshold value.

In some aspects, the system further includes wherein the at least one computer processor is further configured to execute the instructions and to cause the system to perform operations comprising: storing initial patient data in in the at least one storage device; storing the individualized healthcare rules in the at least one storage device; and generating a correspondence between the initial patient data and the individualized healthcare rules.

In some aspects, the system further includes wherein the at least one computer processor is further configured to execute the instructions and to cause the system to perform operations comprising: collecting system usage data of a hearing healthcare education and communication system, the system usage data measuring usage of the hearing healthcare education and communication system by the patient and usage of at least one specific feature of the hearing healthcare education and communication system; comparing the system usage data to a corresponding set of threshold values; determining how the system usage data compares to the corresponding set of threshold values; storing the system usage data and a result of the comparing in the at least one storage device; and based on the result of the determining, determining whether to send the at least one of the message to the patient and the alert to the hearing healthcare provider.

In some aspects, the system further includes wherein the at least one computer processor is further configured to execute the instructions and to cause the system to perform operations comprising at least one of: providing, via the patient computing device, one or more patient reports, wherein the one or more patient reports include a patient presentation of the system usage data; and providing, via the provider computing device, one or more provider reports, wherein the one or more provider reports include a provider presentation of the system usage data.

In some aspects, the system further includes wherein the system usage data includes at least one of: a number of times that features of the system are accessed via the patient computing device, a number of specific features of the system that are accessed via the patient computing device, and a number of specific features of the system that are accessed via the patient computing device within a predetermined period of time.

In some aspects, the system further includes a cloud communications platform configured to, upon a request from the hearing healthcare education and communication system, automatically send outgoing interactive phone messages and text messages to patients and hearing healthcare providers, for reminders and notifications, wherein the cloud communications platform is further configured to receive incoming phone messages and text messages from the patients and the hearing healthcare providers to initiate interactive survey questionnaires, and wherein responses from the patient and the hearing healthcare provider in response to the outgoing messages and the survey questionnaires are stored in the hearing healthcare education and communication system.

In accordance with aspects of the present disclosure, the present disclosure is directed to a method for providing hearing healthcare education and communication, the method comprising: providing, to the patient computing device, a set of education goals related to a hearing aid; transmitting the set of education goals to a display device for display; providing, on the patient computing device, a remote control interface that allows the patient to navigate a hearing healthcare education and communication system and respond to requests from the hearing healthcare education and communication system; receiving from the patient computing device, input data defining a subset of the set of the education goals in response to the set of the education goals displayed on the display device by using the remote control interface; storing the subset of the set of the education goals as personal goals of the patient; providing, to the patient computing device, at least one educational and experiential module related to the personal goals; transmitting the at least one educational and experiential module to the display device for display; determining a hearing aid achievement of the patient, the hearing aid achievement corresponding to at least one of a use of the at least one educational and experiential module by the patient and a level of compliance with the personal goals by the patient; and based on the hearing aid achievement, automatically providing at least one of a message or an alert to bring the patient into compliance with the personal goals.

In some aspects, the method further includes wherein the at least one educational and experiential module includes content review questions, the method further including: providing, to the patient computing device, at least one content review question about content of the at least one educational and experiential module; transmitting the at least one content review question to the display device for display; receiving, from the patient computing device, a patient response to the at least one content review question displayed on the display device by using the remote control interface; comparing the patient response to a correct response; determining if the patient response is a correct response; determining a content review score based on a percentage of correct responses; and based on a result of the determining the content review score, determining whether to send the at least one of the message to the patient computing device and the alert to a hearing healthcare provider computing device.

In some aspects, the method further includes wherein the determining the hearing aid achievement of the patient includes: collecting patient viewing data related to the at least one educational and experiential module; comparing the patient viewing data to a threshold value; based on a result of the comparing, determining how the patient viewing data corresponds to the threshold value; based on the result of the determining; and based on a result of the comparing, determining whether to send the at least one of the message to the patient computing device and the alert to a hearing healthcare provider computing device.

In some aspects, the method further includes at least one of: providing one or more patient reports to the patient computing device, wherein the one or more patient reports include a patient presentation of the patient viewing data; and providing one or more provider reports to the hearing healthcare provider computing device, wherein the one or more provider reports include a provider presentation of the patient viewing data.

In some aspects, the method further includes wherein the at least one educational and experiential module is an educational video, and wherein the patient viewing data includes a cumulative number of different videos viewed on the display device within a predetermined period of time.

In some aspects, the method further includes wherein the determining the hearing aid achievement of the patient further includes: providing, to the patient computing device, a survey question about a hearing aid experience of the patient; transmitting the survey question to the display device for display; receiving, from the patient computing device, a survey response to the survey question displayed on the display device by using the remote control interface; comparing the survey response to a threshold value; determining how the survey response compares to the threshold value; and based on a result of the determining, determining whether to send the at least one of the message to the patient computing device and the alert to a hearing healthcare provider computing device.

In some aspects, the method further includes collecting system usage data of the system, the system usage data measuring usage of the system by the patient and usage of at least one specific feature of the system; comparing the system usage data to a threshold value; determining how the system usage data compares to the threshold value; storing the system usage data and a result of the comparing; and based on the result of the determining, determining whether to send the at least one of the message to the patient computing device and the alert to a hearing healthcare provider computing device.

In some aspects, the method further includes at least one of: providing one or more patient reports to the patient computing device, wherein the one or more patient reports include a patient presentation of the system usage data; and providing one or more provider reports to the hearing healthcare provider computing device, wherein the one or more provider reports include a provider presentation of the system usage data and a recommended adjustment to at least one of the hearing aid.

In some aspects, the method further includes wherein the system usage data includes at least one of: a number of times that features of the system are accessed via the patient computing device, a number of specific features of the system that are accessed via the patient computing device, and a number of specific features of the system accessed via the patient computing device within a predetermined period of time.

In some aspects, the method further includes wherein the at least one educational and experiential module includes troubleshooting information related to a hearing aid problem, the method further comprising: providing, to the patient computing device, troubleshooting questions related to patient experiences using the hearing aid; transmitting the troubleshooting questions to the display device for display; receiving, via the patient computing device, patient responses to the troubleshooting questions displayed on the display device by using the remote control interface; providing troubleshooting advice based on the patient responses to the troubleshooting questions; transmitting the troubleshooting advice to the display device for display; and storing troubleshooting result data based on the patient responses to the troubleshooting questions and success of the patient in resolving the hearing aid problem.

In some aspects, the method further includes at least one of: providing one or more patient reports to the patient computing device based on the troubleshooting result data, wherein the one or more patient reports include a presentation of the troubleshooting result data; and providing one or more provider reports to a hearing healthcare provider computing device based on the troubleshooting result data, wherein the one or more provider reports include a presentation of the troubleshooting result data.

In some aspects, the method further includes wherein the providing the one or more provider reports to the hearing healthcare provider includes: providing the alert to the hearing healthcare provider computing device to alert the hearing healthcare provider of the hearing aid problem experienced by the patient and that the patient has one or more problems with the hearing aid.

In some aspects, the method further includes receiving, via the patient computing device, data from a plurality of users; and separating the data received via the patient computing device according to each of the plurality of users.

In some aspects, the method further includes receiving, via the patient computing device, a request for a callback from a hearing healthcare provider; and transmitting information regarding the request for the callback to at least one of the hearing healthcare provider computing station and a hearing healthcare provider mobile device.

In some aspects, the method further includes wherein the determining the hearing aid achievement of the patient includes: providing, to the patient computing device, progress questions related to a progress of the patient towards achieving each of the personal goals; transmitting the progress questions to the display device for display; receiving, from the patient computing device, patient responses to the progress questions displayed on the display device by using the remote control interface; comparing the patient responses to the personal goals to determine how the patient response compares to the personal goals; and based on a result of the comparing, determining whether to send the at least one of the message to the patient computing device and the alert to a hearing healthcare provider computing device.

In accordance with aspects of the present disclosure, the present disclosure is directed to a system for providing hearing healthcare education and communication, comprising: at least one storage device storing instructions; a media streaming device wirelessly transmitting hearing healthcare education and communication system content from a patient computing device to a display device; and at least one computer processor configured to execute the instructions and to cause the system to perform operations comprising: providing, to the patient computing device, a set of education goals related to a hearing aid; transmitting the set of education goals to the display device for display; providing, on the patient computing device, a remote control interface that allows the patient to navigate the hearing healthcare education and communication system and respond to system requests; receiving from the patient computing device, input data defining a subset of the set of the education goals in response to the set of the education goals displayed on the display device by using the remote control interface on the patient computing device; storing, in the at least one storage device, the subset of the set of the education goals as personal goals of the patient; providing, to the patient computing device, at least one educational and experiential module related to the personal goals; transmitting the at least one educational and experiential module to the display device for display; determining a hearing aid achievement of the patient, the hearing aid achievement corresponding to at least one of a use of the at least one educational and experiential module by the patient and a level of compliance with the personal goals by the patient; and based on the hearing aid achievement, automatically providing at least one of a message or an alert to bring the patient into compliance with the personal goals.

In some aspects, the system further includes wherein the at least one educational and experiential module includes content review questions, and wherein the determining the hearing aid achievement of the patient further includes: providing, to the patient computing device, at least one content review question about content of the at least one educational and experiential module; transmitting the at least one content review question to the display device for display; receiving, from the patient computing device, a patient response to the at least one content review question displayed on the display device by using the remote control interface; comparing the patient response to a correct response; determining if the patient response is a correct response; determining a content review score based on a percentage of correct responses; and based on a result of the determining the content review score, determining whether to send the at least one of the message to the patient computing device and the alert to a hearing healthcare provider computing device.

In some aspects, the system further includes wherein the determining the hearing aid achievement of the patient includes: collecting patient viewing data related to the at least one educational and experiential module; comparing the patient viewing data to a threshold value; based on a result of the comparing, determining how the patient viewing data corresponds to the threshold value; based on the result of the determining; and based on a result of the comparing, determining whether to send the at least one of the message to the patient computing device and the alert to a hearing healthcare provider computing device.

In some aspects, the system further includes wherein the at least one computer processor is further configured to execute the instructions and to cause the system to perform operations comprising at least one of: providing one or more patient reports to the patient computing device, wherein the one or more patient reports include a patient presentation of the patient viewing data; and providing one or more provider reports to the hearing healthcare provider computing device, wherein the one or more provider reports include a provider presentation of the patient viewing data.

In some aspects, the system further includes wherein the at least one educational and experiential module is an educational video, and wherein the patient viewing data includes a cumulative number of different videos viewed on the display device within a predetermined period of time.

In some aspects, the system further includes wherein the determining the hearing aid achievement of the patient further includes: providing, to the patient computing device, a survey question about a hearing aid experience of the patient; transmitting the survey question to the display device for display; receiving, from the patient computing device, a survey response to the survey question displayed on the display device by using the remote control interface; comparing the survey response to a threshold value; determining how the survey response compares to the threshold value; and based on a result of the determining, determining whether to send the at least one of the message to the patient computing device and the alert to a hearing healthcare provider computing device.

In some aspects, the system further includes wherein the at least one computer processor is further configured to execute the instructions and to cause the system to perform operations comprising: collecting system usage data of the system, the system usage data measuring usage of the system by the patient and usage of at least one specific feature of the system; comparing the system usage data to a threshold value; determining how the system usage data compares to the threshold value; storing the system usage data and a result of the comparing in the at least one storage device; and based on the result of the determining, determining whether to send the at least one of the message to the patient computing device and the alert to a hearing healthcare provider computing device.

In some aspects, the system further includes wherein the at least one computer processor is further configured to execute the instructions and to cause the system to perform operations comprising at least one of: providing one or more patient reports to the patient computing device, wherein the one or more patient reports include a patient presentation of the system usage data; and providing one or more provider reports to the hearing healthcare provider computing device, wherein the one or more provider reports include a provider presentation of the system usage data and a recommended adjustment to at least one of the hearing aid.

In some aspects, the system further includes wherein the system usage data includes at least one of: a number of times that features of the system are accessed via the patient computing device, a number of specific features of the system that are accessed via the patient computing device, and a number of specific features of the system accessed via the patient computing device within a predetermined period of time.

In some aspects, the system further includes wherein the at least one educational and experiential module includes troubleshooting information related to a hearing aid problem, and the at least one computer processor is further configured to execute the instructions and to cause the system to perform operations comprising: providing, to the patient computing device, troubleshooting questions related to patient experiences using the hearing aid; transmitting the troubleshooting questions to the display device for display; receiving, via the patient computing device, patient responses to the troubleshooting questions displayed on the display device by using the remote control interface; providing troubleshooting advice based on the patient responses to the troubleshooting questions; transmitting the troubleshooting advice to the display device for display; and storing, in the at least one storage device, troubleshooting result data based on the patient responses to the troubleshooting questions and success of the patient in resolving the hearing aid problem.

In some aspects, the system further includes wherein the at least one computer processor is further configured to execute the instructions and to cause the system to perform operations comprising at least one of: providing one or more patient reports to the patient computing device based on the troubleshooting result data, wherein the one or more patient reports include a presentation of the troubleshooting result data; and providing one or more provider reports to a hearing healthcare provider computing device based on the troubleshooting result data, wherein the one or more provider reports include a presentation of the troubleshooting result data.

In some aspects, the system further includes wherein the providing the one or more provider reports to the hearing healthcare provider includes: providing the alert to the hearing healthcare provider computing device to alert the hearing healthcare provider of the hearing aid problem experienced by the patient and that the patient has one or more problems with the hearing aid.

In some aspects, the system further includes a cloud communications platform configured to, upon a request from the hearing healthcare education and communication system, automatically send outgoing interactive phone messages and text messages to patients and hearing healthcare providers, for reminders and notifications, wherein the cloud communications platform is further configured to receive incoming phone messages and text messages from the patients and the hearing healthcare providers to initiate interactive survey questionnaires, and wherein responses from the patient and the hearing healthcare provider in response to the outgoing messages and the survey questionnaires are stored in the hearing healthcare education and communication system.

In some aspects, the system further includes wherein the at least one computer processor is further configured to execute the instructions and to cause the system to perform operations comprising: receiving, via the patient computing device, data from a plurality of users; and separating the data received via the patient computing device according to each of the plurality of users.

In some aspects, the system further includes wherein the at least one computer processor is further configured to execute the instructions and to cause the system to perform operations comprising: receiving, via the patient computing device, a request for a callback from a hearing healthcare provider; and transmitting information regarding the request for the callback to at least one of the hearing healthcare provider computing station and a hearing healthcare provider mobile device.

In some aspects, the system further includes wherein the determining the hearing aid achievement of the patient includes: providing, to the patient computing device, progress questions related to a progress of the patient towards achieving each of the personal goals; transmitting the progress questions to the display device for display; receiving, from the patient computing device, patient responses to the progress questions displayed on the display device by using the remote control interface; comparing the patient responses to the personal goals to determine how the patient response compares to the personal goals; and based on a result of the comparing, determining whether to send the at least one of the message to the patient computing device and the alert to a hearing healthcare provider computing device.

DETAILED DESCRIPTION

Figure 1:
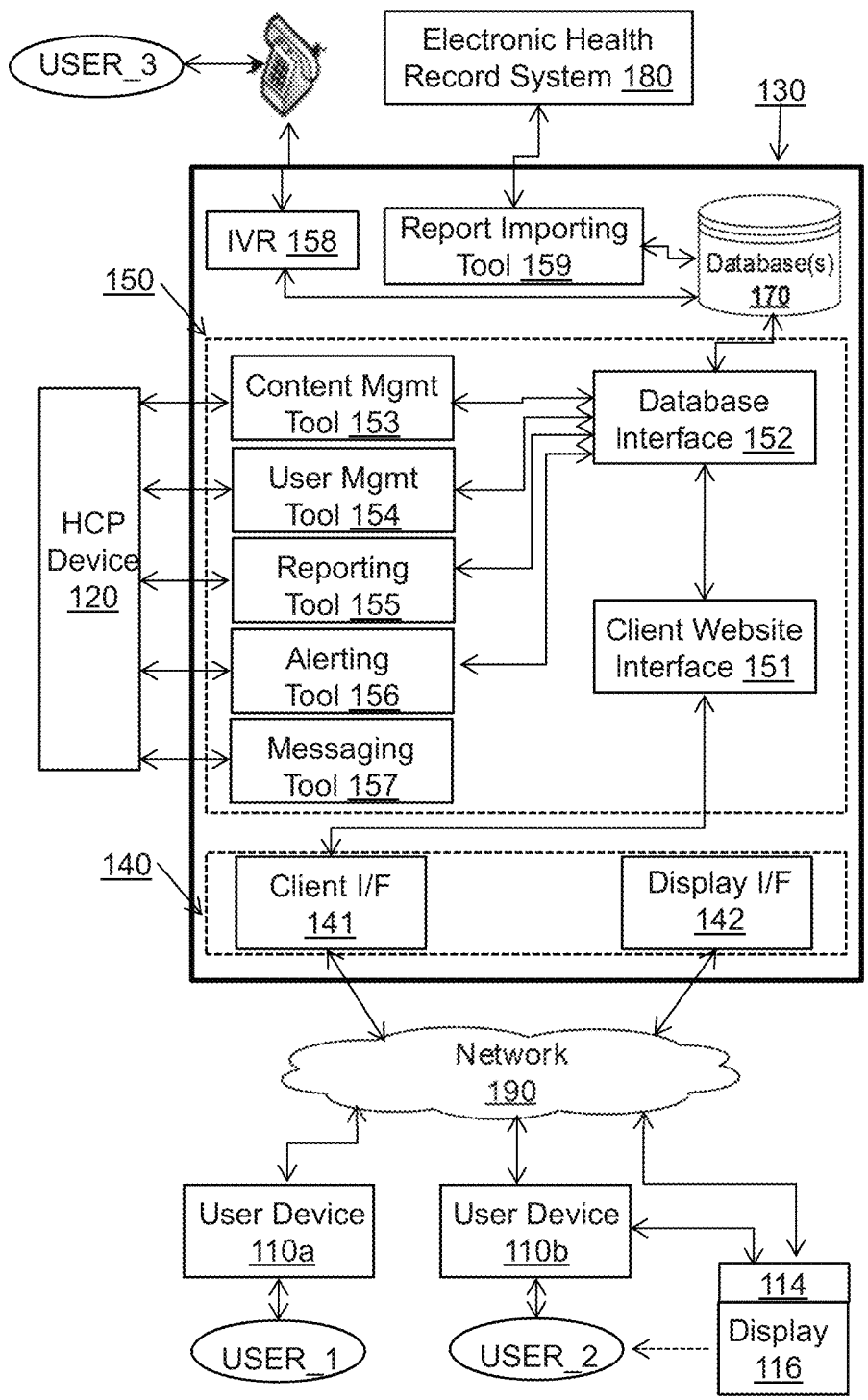
FIG. 1 is a diagram illustrating an exemplary hearing healthcare system for providing education, communication, and tracking of hearing healthcare, according to certain disclosed embodiments.

Disclosed embodiments comprise an integrated system called TELLYHEALTH™ that is a combination of a computer server that provides a website and data for the hearing care professional, a website for use by hearing care professionals, a patient's computing device, a telephone, a streaming device, a Wi-Fi system, and either a television (TV) set or a computer monitor with a connected speaker. TELLYHEALTH™ is a reference to the provision of personalized hearing healthcare education and aftercare to patients via their television ("Telly" in British parlance) as part of an integrated system. The TELLYHEALTH™ system (to be herein referred to as "the System") is designed for ease of use and ease of viewing by older adults, as well as ease of viewing by groups of individuals.

A hearing care professional (HCP) uses a computing device to log in to a secure "HCP website" that is hosted by one or more servers which may be in the cloud. In some embodiments, the secure HCP website may be hosted by a hosting service, such as, for example Amazon Web Services. The hosted HCP website may be referred to herein in the singular although it may be embodied by several networked servers and/or other computing devices. The HCP website may be formed of one or more modules or "tools." As is traditional in the field of the disclosed technology, features and embodiments are described, and illustrated in the drawings, in terms of functional blocks, units, tools, and/or modules. Those skilled in the art will appreciate that these blocks, units, tools, and/or modules are physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units, tools, and/or modules being implemented by microprocessors or similar, they may be programmed using software (e.g., microcode) to perform various functions discussed herein and may optionally be driven by firmware and/or software. Alternatively, each block, unit, tools, and/or module may be implemented by dedicated hardware, or as a combination of dedicated hardware to perform some functions and a processor (e.g., one or more programmed microprocessors and associated circuitry) to perform other functions. Also, each block, unit, tools, and/or module of the embodiments may be physically separated into two or more interacting and discrete blocks, units, tools, and/or modules without departing from the scope of the inventive concepts. Further, the blocks, units, tools, and/or modules of the embodiments may be physically combined into more complex blocks, units, tools, and/or modules without departing from the scope of the inventive concepts.

The HCP website is designed to enable an HCP to enroll patients in the System with personalized information about the patient and his/her hearing aid. The HCP website is also designed to: (a) track the enrolled patient's progress using their hearing aid and applying new communication skills, and (b) empower the HCP to provide efficient, effective, and timely patient "aftercare" with the assistance of data provided by the System. The HCP website accomplishes these goals by accessing databases related to: (a) the patient's hearing aid use and care, (b) System-provided hearing aid education, and (c) other aspects of System use relative to objectives established by the HCP.

FIG. 1 is a diagram illustrating an exemplary hearing healthcare system for providing education, communication, and tracking of hearing healthcare, according to certain disclosed embodiments.

As shown in FIG. 1, an exemplary hearing healthcare system 100 may include a plurality of user devices 110 (e.g., user device 110a and user device 110b), a display device 116, at least one hearing healthcare provider (HCP) device 120, and a hearing healthcare provision (HHP) server 130.

User devices 110 may be any type of electronic computing device and/or component configured to execute one or more processes, many of which are known in the art. User devices 110 can include, by way of example and not limitation, clients, desktop computers, laptop computers, network computers, workstations, personal digital assistants (PDA), tablet computers and/or electronic readers (e.g., iPad, Kindle Fire, Playbook, Touchpad, etc.), telephony devices, smartphones, etc. In one example embodiment, one or more user devices 110 may be mobile computing devices. User devices 110 may be configured to transmit and/or receive information to and/or from other user devices 110, HHP server 130, and/or display device 116 directly and/or indirectly via any combination of wired and/or wireless communication systems, method, and devices, including, for example, network 190. User devices 110 may receive input from, and provide output to, one or more of a patient, a caregiver for the patient, or a friend or family member of the patient.

Figure 2:
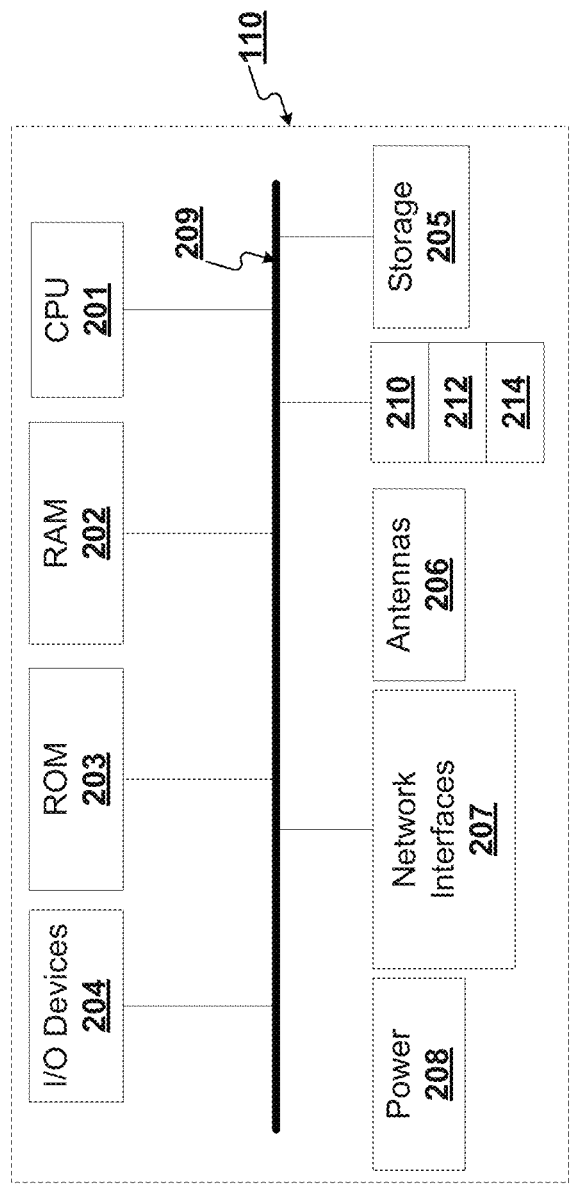
FIG. 2 is a block diagram of an example user device, consistent with certain disclosed embodiments.

FIG. 2 is a block diagram of an example user device 110, consistent with certain embodiments. It should be readily apparent that the example user device 110 depicted in FIG. 2 represents a generalized schematic illustration and that other components/devices can be added, removed, or modified. In one example embodiment, user device 110 can be configured to include address translation and full virtual-memory services.

As shown in FIG. 2, each user device 110 can include one or more of the following components: at least one central processing unit (CPU) 201 configured to execute computer program instructions to perform various processes and methods, random access memory (RAM) 202 and read only memory (ROM) 203 configured to access and store data and information and computer program instructions, I/O devices 204 configured to provide input and/or output to client computing device 110 (e.g., keyboard, mouse, display, speakers, printers, modems, network cards, etc.), and storage media 205 or other suitable type of memory (e.g., such as, for example, RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives, any type of tangible and non-transitory storage medium), where the files that comprise an operating system 210, application programs 212 including, for example, web browser application, email application and/or other applications, and data files 214 are stored.

In addition, each user device 110 can include antennas 206, network interfaces 207 that provide wireless and/or wire line digital and/or analog interface to one or more networks, such as network 150, over one or more network connections (not shown), a power source 208 that provides an appropriate alternating current (AC) or direct current (DC) to power one or more components of user device 110, and a bus 209 that allows communication among the various disclosed components of the user device 110 of FIG. 2. Each of these components is well-known in the art and will not be discussed further.

In one or more exemplary designs of user device 110 of FIG. 2, the functions described can be implemented in hardware, software, firmware, or any combination thereof. If implemented in software, the functions can be stored as one or more instructions or code on computer-readable medium, including the computer-readable medium described above (e.g., RAM 202, ROM 203, storage media 205, etc.). The term "software" may refer to prescribed rules to operate a computing device. Examples of software may include: software; micro-code; code segments; instructions; applets; pre-compiled code; compiled code; interpreted code; computer programs; and programmed logic.

Figure 3:
FIG. 3 is an example welcome screen displayed on a display device of a hearing healthcare system, according to certain disclosed embodiments.
Figure 4:
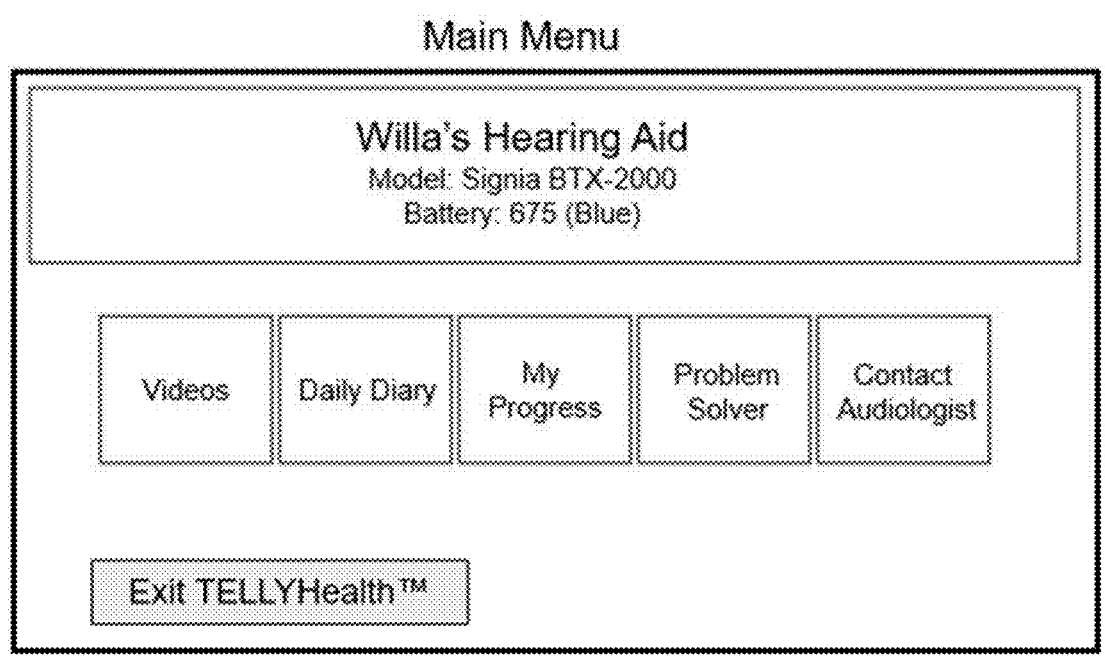
FIG. 4 is an example main menu screen displayed on a display device of a hearing healthcare system, according to certain disclosed embodiments.

In some embodiments, application programs 212 can include an application programming interface (API), such as a casting API. The casting API may be a set of software instructions that cause the user device 110 to send data to a display device (e.g., display device 116 of FIG. 1), causing the display device 116 to display Patient Display Portal Screens. Exemplary Patient Display Portal Screens are illustrated in FIGS. 3 and 4.

Figure 5:
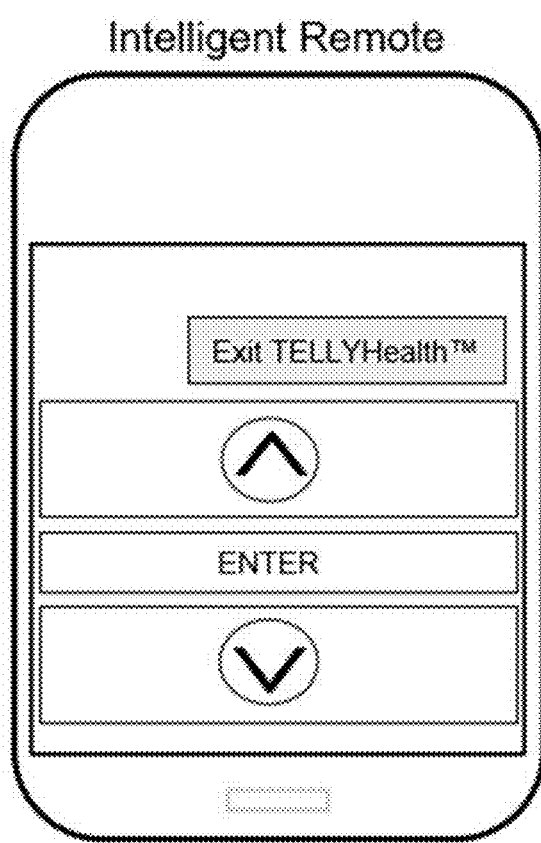
FIG. 5 is an example Intelligent Remote screen, according to certain disclosed embodiments.

In addition, in some embodiments, application programs 212 of the user device 110 may include an intelligent remote application. Upon execution, the intelligent remote application may provide an Intelligent Remote. For example, the Intelligent Remote (see FIG. 5) may be comprised of the user device 110 with a touchscreen configured to provide one or more "virtual buttons" or icons that are used to operate and navigate the screens of the HCP website of hearing healthcare system 100 and, in particular, the presently visible and active screen on the display device 116. For example, the user may tap on one virtual button of the Intelligent Remote to perform an action such as entering a number or navigating to another screen.

Returning to FIG. 1, the hearing healthcare system 100 may include a display device 116. The display device 116 may include a display screen used to provide visual output from a computer, cable box, video camera, VCR, or other video generating device. The display device 116 may be, for example, a digital or analog television, a digital or analog computer monitor, etc. In some embodiments, the display device 116 may include a streaming device to exchange information with user device 110 and/or HHP server 130. For example, the display device 116 may include a GOOGLE™ CHROMECAST™ device and associated sender and receiver APIs that cause mobile media data to be displayed on the display device 116. The sender and receiver APIs may include functions to interact with the sender (e.g., user device 110, HHP server 130) or media content and to work with the receiver or the display device 116. The sender API may include parameters for configuration, requests, and all that is related to media (volume, display, TV show). The receiver API may include parameters for cast receiver, media playback, and possible properties (connected, inactivity, standby). Available index of all classes and functions. In some embodiments, the user device 110 and display device 116 may communicate with one another using the CHROMECAST™ device. For example, the casting API of the user device 110 may cause the display device 116 to display media that is provided from the HHP server 130 via network 190 to the CHROMECAST™ device.

HCP device 120 may be any type of electronic device and/or component configured to execute one or more processes, many of which are known in the art. HCP device 120 can include, by way of example and not limitation, clients, desktop computers, laptop computers, network computers, workstations, personal digital assistants (PDA), tablet computers and/or electronic readers, telephony devices, smartphones, etc. HCP computing device 120 may be configured to transmit and/or receive information to and/or from other HCP computing devices 120, HHP server 130, and/or electronic health records system 180 directly and/or indirectly via any combination of wired and/or wireless communication systems, method, and devices, including, for example, network 190. HCP devices 120 may receive input from, and provide output to, one or more of a hearing healthcare provider or other authorized personnel (e.g., third-party administrator, etc.).

HHP server 130 can be one or more physical computers, or computer systems, configured to run one or more services to support users of other computers on one or more networks and/or computer programs executing on physical computers, or computer systems, and configured to serve the requests of other programs that may be operating on one or more servers (not shown) or on other computing devices, such as user devices 110, display device 116, HCP device 120, and/or electronic health record system 180. HHP server 130 can include, by way of example and not limitation, communication servers, database servers, fax servers, file servers, mail servers, print servers, name servers, web servers, proxy servers, gaming servers, etc. In some aspects, HHP server 130 may be configured to transmit and/or receive information to and/or from user computing devices 110, display device 116, HCP device 120, other servers (e.g., HHP server 130, Internet Service Provider (ISP) servers (not shown), etc.), electronic health records system 180, and/or databases directly and/or indirectly via any combination of wired and/or wireless communication systems, method, and/or devices, including, for example, network 190. HHP server 130 may include one or more physical servers, or server systems, and/or one or more proxy servers, each configured to run one or more services to support other computers or computer systems, such as, for example, client computer systems (not shown). In certain embodiments, the same server devices may perform the roles of a physical HHP server 130 and/or a proxy HHP server 130.

HHP server 130 can include a set of client components 140, such as a client interface 141 and a display interface 142. The client interface 141 may include both software and hardware components to facilitate data communications between the HHP server 130 and the user device 110. For example, training, education, or troubleshooting information may be transmitted from the HHP server 130 to the user device 110, or data from the patient's hearing aid may be transferred to the HHP server 130 via the user device 110. Data communications may include providing a HHP website the user device 110 and receiving input relate to the HHP website.

The display interface 142 may include both software and hardware components to facilitate data communications between the HHP server 130 and the display device 116. For example, the HHP server 130 may transmit media data directly from the HHP server 130 to the display device 116, and receive information about viewing of the media data from the display device 116. In some embodiments, the display interface 142 may be configured to cause the HHP website to be displayed on the display device 116.

HHP server 130 can further include a set of administration components 150, such as a client website interface 151, a database interface 152, a content management tool 153, a user management tool 154, a reporting tool 155, an alert tool 156, and a messaging tool 157. Client website interface 151 may include both software and hardware components to facilitate data communications between the client interface 141 and a database interface 152.

The client website interface 151 may include both software and hardware components to facilitate data communications between the client interface 141 and the database interface 152. For example, the client interface 141 may transmit data from the user device 110 to the database interface 152 for subsequent storage in one or more databases 170, and may receive data stored in the one or more databases 170 via the database interface 152 for subsequent transmission to the user device 110. Communication between the client interface 141 and the user device 110 may be facilitated by an HCP website. For example, information (e.g., patient input data) may be transmitted from the user device 110 to the HHP server 130 by inputting the data into structured fields of the HCP website, and data or other information (e.g., messages, instructions, reminders, videos, flowcharts, etc.) may be provided to the user by presenting the data or information on the HCP website. The HCP website may be displayed on display device 116, and an Intelligent Remote may be used to navigate the HCP website, as discussed further herein.

The database interface 152 may include both software and hardware components to facilitate data communications between one or more of the client website interface 151, the content management tool 153, the user management tool 154, the reporting tool 155, the alert tool 156, the messaging tool 157, and databases 170.

Each of the content management tool 153, the user management tool 154, the reporting tool 155, the alert tool 156, and the messaging tool 157 may be formed by a software application operating on HCP server 130, another computing device external to the HCP server 130 accessible by the HCP server 130, or other configurations described herein. These software applications may be stored separately from each other or may share resources.

The content management tool 153 may transmit data to and receive data from one or more databases 170 via the database interface 152. For example, the content management tool 153 may receive input from one or more HCP devices 120, and transmit the input to the database interface 152 for storage in the one or more databases 170. In some embodiments, the content management tool 153 may be used by authorized personnel for adding, deleting, and editing training and education content of the hearing healthcare system 100 without requiring assistance from IT personnel—thus reducing the process response time and associated support costs for the hearing healthcare system 100. Hearing healthcare system 100 content may include videos, text, and multimedia content that is used for patient education or training, evaluating patient knowledge on a topic, supplies and equipment available for sale to the patient, and other content that may support the patient with hearing aids and the patient's family, friends and caregivers.

The user management tool 154 may transmit data to and receive data from one or more databases 170 via the database interface 152. For example, the user management tool 154 may receive input from one or more HCP devices 120, and transmit the input to the database interface 152 for storage in the one or more databases 170. In some embodiments, the user management tool 154 may be used by the HCP to enter the patient's data, including details of the patient's hearing aid, and to configure their assigned patients with access to the hearing healthcare system 100. The user management tool 154 may also be used by the HCP to add and delete other users of the hearing healthcare system 100 and their offices and organizations and edit their enrollment information. The user management tool 154 may also be used to customize a patient portal for each patient based on entered parameters such as their hearing aid style and personalized alert thresholds. The user management tool 154 may also be used to download the data for a particular patient or group of patients or a particular HCP or group of HCPs. The user management tool 154 can also be used as a user support tool for individuals providing support for HCPs and patients. For example, a HCP may enroll a new patient in the hearing healthcare system 100 via the HCP device 120 using the user management tool 154 once the patient selects, but before they receive, their hearing aids. At this point in time, only a specified subset of the training and educational content of the hearing healthcare system 100 may be activated via the user management tool 154. After the hearing aid fitting, the HCP may use the user management tool 154 to activate the remaining training and educational content. Such activation may include setting access controls to additional training and educational content and setting one or more thresholds related to education, training, tracking, and communication of the hearing healthcare patient.

The reporting tool 155 may transmit data to and receive data from one or more databases 170 via the database interface 152. For example, the reporting tool 155 may receive input from one or more HCP devices 120, and transmit the input to the database interface 152 for storage in the one or more databases 170. In some embodiments, the reporting tool 155 may be used by the HCP to assemble, view and download reports about usage of the hearing healthcare system 100 among all their assigned patients, as a group, and for each individual patient. The reports provide clinically important information on the patient's hearing aid use and care experiences, thereby enabling the HCP to rapidly focus on the patient's needs and provide ongoing and active care of the patient. Reports may be aggregated by, for example: (a) all companies using the hearing healthcare system 100, (b) all offices within an individual company using the hearing healthcare system 100, (c) individual offices within a company using the hearing healthcare system 100, and (d) all patients within an office using the hearing healthcare system 100. One or more of the individual patient reports may also be posted on the Patient-TV Portal and accessed by that individual patient and by other authorized users. The reporting tool 155 may also be used by an authorized user to assemble, view and download reports about usage of the hearing healthcare system 100 among all HCP users, as a group, and for each individual HCP user.

Each of the alerting tool 156 and the messaging tool 157 may transmit data to and receive data from one or more databases 170 via the database interface 152. For example, the alerting tool 156 and/or the messaging tool 157 may receive input from one or more HCP devices 120, and transmit the input to the database interface 152 for storage in the one or more databases 170. The alerting tool 156 may be used by the HCP to set customized alert thresholds for each patient, post patient alerts on the HCP website for transmission to the patient via the user device 110 and/or display device 116. In addition, the alerting tool 156 may direct the messaging tool 157 to send electronic or voice messages to the HCP about a new alert or a new series of alerts. The alerts enable the HCP to easily track instances and trends of the patient's hearing aid and use experiences of the hearing healthcare system 100 by the patient or other user (e.g., patient caregiver, patient family member, patient friend, etc.).

For example, the alerting tool 156 can track and evaluate the patient's ability or inability to use their hearing aids successfully and automatically, based on data transferred wirelessly from the patient user device 110 or from their hearing aid to the HHP server 130. In some embodiments, the patient's ability or inability to user a hearing aid successfully may be tracked and evaluated based on the patient's inputs to a Patient Daily Diary. Inputs to the Patient Daily Diary may be provided via the user device 110 and/or display device 116.

As an example, the alerting tool 156 allows the HCP to select a threshold of the minimum number of hours of daily hearing aid use expected of the patient for a specific number of consecutive days. The alerting tool 156 then compares the patient's self-report data on their actual number of daily hours of hearing aid use over the consecutive day range to the threshold value. The patient's self-report data may be input by the user via the user device 110 and/or display device 116, and then transmitted to the HHP server 130. If the actual hours value is less than the threshold value over the specified range of days, the alerting tool 156 will trigger an alert that is stored in one or more databases 170 of the HHP server 130 and is also sent to the HCP as an electronic message via e-mail, texting, voice (e.g., phone message), or another suitable communication channel. The HCP then records contacts with the patient (e.g., office visit or phone call) that are intended to resolve the alert and then records the actual resolution of the alert (e.g., patient buys new hearing aid batteries, so they can resume using their hearing aids) on the HHP server 130. In another example, an alert may be triggered by the hearing healthcare system 100 if the patient uses the hearing healthcare system 100 (e.g., Patient-TV Portal and/or inbound Messaging System, which are discussed further herein) less frequently than the threshold set by the HCP via the hearing healthcare system 100. Patient use of the hearing healthcare system 100 is automatically tracked by the hearing healthcare system 100 each time the patient logs into the hearing healthcare system 100 and, for example, completes a task on the hearing healthcare system 100 by selecting at least one menu. Additionally, the alerting tool 156 may be used to monitor the pace of the patient completing tasks on the hearing healthcare system 100 as defined by the HCP with the individualized healthcare rules. If the patient is not keeping up with the requested task completion pace and/or schedule, the messaging tool 157 may send out a personalized message to such patient with instructions to help the patient get back on track or to bring the user into compliance with the individualized healthcare rules input by the HCP.

The messaging tool 157 may be directed by one or more other tools (e.g., the content management tool 153, the user management tool 154, the reporting tool 155, the alert tool 156) to automatically send out targeted messages by e-mails, text messages (i.e., SMS), or interactive voice response (IVR) telephone call messages to the patient, the HCP, or another designated individual. These messages may be generated by a commercially available cloud-based server that is designed for interactive inbound and outbound communications with subscribed individuals such as HCPs, patients, and other individual who are enrolled in the hearing healthcare system 100 by the HCP or another authorized person. Outbound patient messages are scheduled by the HCP via the HCP device 120 in consultation with the patient. The scheduled outbound patient messages may be included in the individualized healthcare rules which are stored in databases 170.

In one example embodiment, the messaging tool 157 may remind the patient to use the hearing healthcare system 100 when the patient's usage, as tracked by the hearing healthcare system 100 via the reporting database, does not meet the usage goals established by the patient in concert with the HCP and stored in the HHP server 130 via the HCP device 120. The usage goals may include frequency of accessing the hearing healthcare system 100, viewing certain videos within a prescribed time period, evaluating progress towards the patient's personal goals, or another measure that the HCP enters into the HCP website. Based on the patient's shortfalls in achieving the desired use of the hearing healthcare system 100, the messaging tool 157 may provide outbound messages in the form of reminders that encourage the patient to derive more value from the hearing healthcare system 100. As the patient gains experience with the hearing healthcare system 100 by, for example, navigating menus and entering data into the hearing healthcare system 100, the nature of the outbound reminder messages may change. In some cases, based on these parameters, the patient will stop receiving outbound reminder messages. In other cases, the patient data will trigger new outbound reminder messages.

Figure 6:
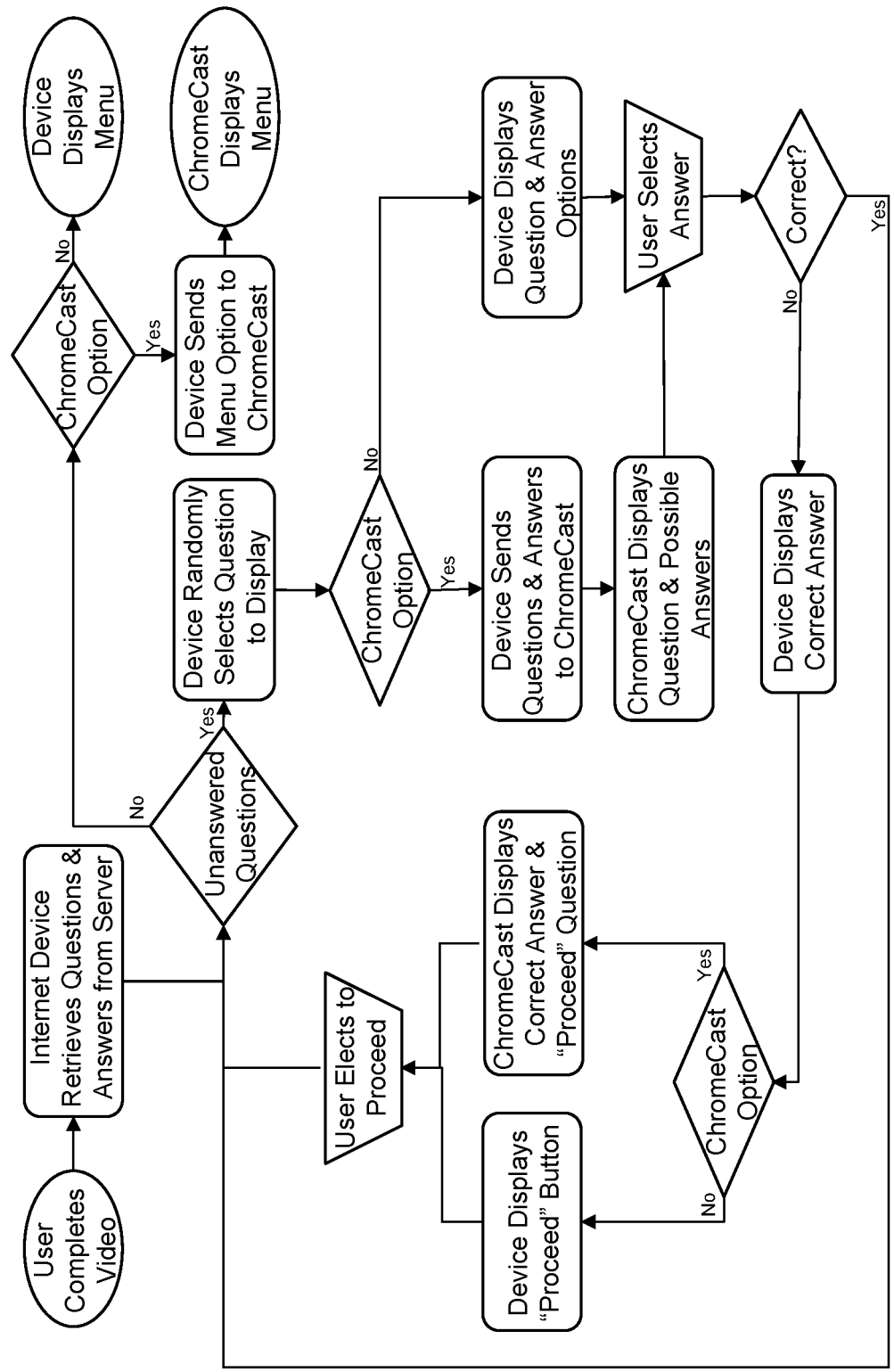
FIG. 6 is an example flowchart of a video review quiz process, according to certain disclosed embodiments.

In another example embodiment, the messaging tool 157 may assist the patient in identifying specific subject areas that require reinforcement. The hearing healthcare system 100 may include algorithms for intelligently analyzing the patient's responses to video review questions and patient daily diary questions and use of the problem solver in order to provide targeted outbound messages that provide targeted education for the patient and reinforce new information presented to the patient (see FIG. 6).

The messaging tool 157 may also include an inbound messaging feature where it is accessed by a patient who either calls in or "texts in" to the hearing healthcare system 100. In one example embodiment, the patient may use this inbound capability of the messaging tool 157 to complete the patient daily diary questions by phone or text rather than by using the Patient-TV Portal. For example, a user (e.g., USER_3) may interact with the HHP server 130 via a telephony device and an IVR system 158. The patient's daily diary responses through this means will be reported on the HCP website and Patient-TV Portal as if they were entered via the display 116 using the Intelligent Remote. In alternative embodiments, the patient may use the inbound messaging tool 157 to access other content of the hearing healthcare system 100, to obtain hearing aid troubleshooting guidance, to respond to other questions of the hearing healthcare system 100, or to leave a message for the HCP.

The messaging tool 157 may further send out an alert message to the HCP when the alerting tool 156 is activated. When the HCP receives such an alert message in the form of an e-mail, automated IVR phone call, or text message, the HCP may contact the patient or first review the details of the alert on the HCP website and then contact the patient. The HCP will then record on the HCP website when the HCP: (a) contacts the patient to discuss the issue that triggered the alert, and (b) resolves the alert in concert with the patient. The HCP also may enter clinical notes related to patients to the HHP server 130 via the HCP device 120 for storage in one or more databases 170.

The HHP server 130 may further include an IVR system 158 and a report importing tool 159. In some embodiments, the IVR system 158 may initiate telephone call messages to the patient, the HCP, or another designated individual. For example, the IVR system 158 may transmit alert messages to the patient, the HCP, or another designated individual, in response to instructions from the messaging tool 157. In other embodiments, the IVR system 158 may receive patient input (e.g., completing the patient daily diary questions by phone or text), and the IVR system 158 may transmit the received patient input to the databases 170 for storage. As illustrated in FIG. 1, the IVR system 158 may communicate with a user USER_3 via a telephony device (e.g., telephone, smart phone, etc.).

Report importing tool 159 may access the electronic health record system 180, and download stored healthcare information related to one or more patients and/or upload healthcare information related to one or more patients for storage on the electronic health record system 180. In some embodiments, for example, the record importing tool 159 may export patient healthcare data to the electronic health record system 180, the healthcare data including identification of hearing aid(s) worn by the patient, individualized healthcare rules and corresponding threshold values for the patient, input data received by the HHP server 130 from the user device 110 (e.g., Daily Diary inputs, etc.), tracking data related to the patient, HHP server 130, and the hearing healthcare system 100.

Electronic health record system 180 may include one or more computing devices configured to store databases, e.g., organized collections of data and their data structures, and/or execute database management systems, e.g., computer programs configured to control the creation, maintenance, and use of the database. Electronic health record system 180 may store health records related to one or more patients.

In addition, the HHP server 130 may include one or more databases. Databases 170 can be one or more computing devices configured to store databases, e.g., organized collections of data and their data structures, and/or execute database management systems, e.g., computer programs configured to control the creation, maintenance, and use of the database. Collectively, databases and their database management systems can be referred to as database systems. As used herein, database 170 can refer to databases, database management systems, and/or database systems. In some aspects, database 170 can be configured to store databases, while database management systems are stored and executed on one or more other computing devices, such as HHP server 130. In one implementation, databases 170 can include software database programs configured to store data associated with HHP servers 130 and their associated applications or processes, such as, for example, standard databases or relational databases. Databases 170 can include relationship database management systems (RDBMS) that may be configured to run as a server on HHP servers 130. In some embodiments, databases 170 can be configured to transmit and/or receive information to and/or from user computing devices 110, HCP computing devices 120, HHP servers 130, and/or other databases 170 directly and/or indirectly via any combination of wired and/or wireless communication systems, method, and/or devices, including, for example, network 190.

Databases 170 may include, for example, a patient database, an HCP databases, a hearing aid, ancillary equipment, and supplies database, a system content database, a messaging database, an alerts database, a reports database, a troubleshooting database, an organizational database, an appointments database, etc.

The patient database may be comprised of data entered by the HCP about each patient enrolled in the hearing healthcare system 100, including their name, contact information, associated HCP, and hearing aid information. The HCP database may be comprised of data about the HCPs enrolled in the hearing healthcare system 100, including their name, contact information, work locations, and licensing or other authorizing information. The hearing aid, ancillary equipment and supplies database may be comprised of information about commercially-available hearing aid models (e.g., specification and other technical information) and related hearing aid products and supplies that may be used by patients or HPCs enrolled in the hearing healthcare system 100.

The system content database may be comprised of hearing aid use and care content and communications education content in the form of text, videos, audio messages, still photographs, multimedia, and flow charts. Examples of hearing aid use and care content and communications education content stored in the system content database may include, for example: introduction to the system and system training; personal goal setting, which provides for selecting preferred goals and evaluating progress on each selected goal on the system; system-selected videos that are specific to the patient's hearing aid style for training on inserting and removing hearing aids; hearing aid maintenance tips based on the patient's hearing aid style; hearing aid use tips based on the patient's hearing aid style; medical issues related to hearing aid use (e.g., ear wax, tinnitus, etc.); advanced hearing aid use tips (e.g., home, landline phones, cells phones, theaters, restaurants, lecture halls, etc.), including selection of the hearing assistive technologies for different environments; communication strategies; identification/ resolution of communication problems; etc. Details about the patient's access of, and feedback to, the various may also appear on the HCP's website and be accessible to the HCP.

The messaging database may be comprised of inbound and outbound messages that are transmitted between the HCP, patients, and the HHP server 130 on an ad hoc basis or on a schedule that is entered into the hearing healthcare system 100. For example, inbound messages may be messages that are transmitted from a HCP, patient, or other person to the HHP server 130, and outbound messages may be messages that are transmitted from the HHP server 130 to an HCP, patient, or other person. One or more messages may be triggered by data that has been entered into the hearing healthcare system 100 by the HCP or the patient or the message may be automatically generated. Examples of message types and triggers stored in the messaging database include: use/access of Daily Diary, triggered when patient has not evaluated his/her progress on his/her goals for a predetermined number of days; use/access of training materials, triggered when patient has not viewed training material provided by the hearing healthcare system 100 at a predefined pace (e.g., number of videos within or over predefined number of days, etc.); comprehension/understanding of training materials, triggered when patient responds incorrectly to maximum number of the video review questions on their first viewing of a video, and reinforcement/reviewing is recommended; etc. The messages may be personalized by inserting variables representing the predefined numbers of days, uses, engagements, into a personalized message by the hearing healthcare system 100 based on data stored therein or can be default values that can be changed by the HCP, the patient, etc. In some embodiments, the variables can be changed by the HCP as part of the individualized healthcare rules and corresponding threshold values.

The alerts database may be comprised of rules that trigger alerts and the actual alert messages that are sent to the HHP server 130 or to the HCP via an e-mail, text or telephone/ voice message. In some embodiments, the alerts database may include alert messages that correspond to certain types of messages in the messaging database. For example, when a Type 6 message is triggered, an alert message may also be triggered to notify the HCP that the patient is struggling to comprehend the training material. Other alerts may be triggered, for example, when a patient requests a call back from the HCP (e.g., to answer questions); when a patient does not wearing their hearing aids for the defined minimum number of hours per day; when a patient is experiencing discomfort with their hearing aid; when the patient's experience of hearing aid sound quality in doors (e.g., rated on a 5-point Likert scale) does not meet the goal established by the HCP; when a patient is not accessing and/or using the hearing healthcare system 100 at the minimum frequency determined by the HCP through the individualized healthcare rules; etc.

The reports database may be comprised of compilations of data and graphical and tabular reports associated with each HCP and patient based on the HCP's and patient's use of the hearing healthcare system 100 and their data inputs or responses. For example, the reports database may store initial data about a patient as initial patient data (e.g., name, date of birth, height/weight, relevant health information, hearing aid(s) used by patient, etc.). In addition, the reports database may store individualized healthcare rules including individualized healthcare rule categories defining one or more patient instructions and goals specific to an individual patient and thresholds for each of the individualized healthcare rules. Examples of individualized healthcare rule categories and corresponding threshold values include (with modifiable variables represented by "< >"): video viewing, having a threshold defining a minimum <number> of videos within <number> of days; patient comprehension/understanding, having a threshold defining a minimum <percentage> of response questions answered correctly; patient comfort wearing the hearing aid, having a threshold defining a minimum <rating> for <left/right> hearing aid; quality of patient's experience when wearing the hearing aid, having a threshold defining a minimum <rating> for sound quality of the hearing aid; number of hours per day that a hearing aid is worn by the patient, having a threshold defining a minimum of <number> hours each day; etc.

The reports database may further store data user input data. The user input data may include, for example, personal goals, responses to personal goal assessment questions, tracking of user viewing of training or education videos, responses to questions following training or education videos, daily diary inputs, etc. The initial input data and the individualized healthcare rules may be input by the HCP via the HCP device 120. The user input data may be input by a patient, patient family member or friend, or patient caregiver via the user device 110. The reports may be provided to the HCP via the HCP device 120 and/or the user via the user device 110. The hearing healthcare system 100 can be configured to send reports on the patient's goals and progress, as well as related alerts and analysis, to the HCP and caregivers, approved healthcare systems, family members, by e-mail, text messages, or automated voice (IVR) phone calls.

The troubleshooting database may be comprised of potential hearing aid problems and corresponding flow charts of possible solutions for each problem. The organizational database may be comprised of information on organizations (e.g., hospitals, healthcare chains, private practices, etc.) that use the hearing healthcare system 100 to assist their HCPs in providing hearing healthcare to patients. The appointments database is comprised of the HCP's schedule, openings for appointments, and appointments made by patients who use the hearing healthcare system 100.

Referring to FIG. 1, network 190 may be any appropriate network or other communication link that allows communication between or among one or more computing systems and/or devices, such as, for example, user devices 110, display device 116, HCP devices 120, HHP servers 130, etc. Network 190 may be wired, wireless, or any combination thereof. Network 190 may include, for example, the Internet, a local area network, a wide area network, a WiFi network, a workstation peer-to-peer network, a direct link network, a Bluetooth connection, a bus, or any other suitable communication network or any combination thereof.

Although FIG. 1 depicts HHP servers 130 as communicating with user devices 110 and HCP devices 120 using an indirect network connection, such as a connection through network 190, those skilled in the art will appreciate that HHP servers 130 may also communicate with user devices 110 and HCP devices 120 using a direct communications link or a communications link separate from network 190. In the embodiment of FIG. 1, user devices 110 and HCP devices 120 may communicate directly with HHP servers 130 via network 190 using standard Internet Protocols, such as HTTP, transmission control protocol (TCP), internet protocol (IP), etc. For example, HTTP requests from user devices 110 and HCP devices 120 may be encapsulated in TCP segments, IP datagrams, and Ethernet frames and transmitted to HHP servers 190. In some embodiments, third parties may participate as intermediaries in the communication, such as, for example, Internet Service Providers (ISPs) or other entities that provide routers and link layer switches. Such third parties may not, however, analyze or review the contents of the Ethernet frames beyond the link layer and the network layer, but instead analyze only those parts of the packet necessary to route communications from user devices 110 and HCP devices 120 to HHP servers 120.

Herein, for ease of discussion, the term "Patient-TV Portal" is used to refer to a combination comprised of (a) user device 110, (b) display device 116, (c) the streaming device (e.g., CHROMECAST™), and (d) network 190. The Patient-TV Portal may be used by the patient to access all of the educational and aftercare features of the System and to enter important data into the System. The user may use the Patient-TV Portal to access all of the educational and aftercare features of the hearing healthcare system 100 and to enter data into the hearing healthcare system 100.

In an example embodiment including a TV as the display device 116, the patient sets up the Patient-TV Portal in the home as follows: The patient may connect the streaming device to a port, such as an HDMI port, on the TV or monitor and connects the streaming device to a power source. Then the patient may set up the Patient-TV Portal by configuring the streaming service on their patient computing device and configuring both the streaming device and the patient's computing device to use the same local Wi-Fi system. The patient may enter the internet address of the HHP server 130 provided by the HCP on the user device 110, and create an HHP icon on a main screen of the user device 110. Then the patient may tap on the HHP icon and enter the password assigned by the HCP (which can be changed by the patient later via the Patient-TV Portal). Then the patient may tap on one or more special buttons to log in to the Patient-TV Portal. At this point: (a) the Patient-TV portal is integrated with the HCP website and the HHP server 130 through the user device 110 and the associated HHP server 130 tools and databases described earlier, (b) the Welcome screen is streamed to the TV (see FIG. 3), and (c) the Intelligent Remote buttons appear on the patient's user device 110 (see FIG. 5). After the patient selects an option on the Welcome Screen using the Intelligent Remote, the Patient-TV Portal's Main Menu appears on the patient's TV (see FIG. 4).

As discussed above, the user may utilize the Intelligent Remote to interact with the data or other media displayed on the display device 110. For example, the user may tap on one virtual button of the Intelligent Remote to perform an action such as entering a number or navigating to another screen. The Patient-TV Portal then performs the desired action. When the HHP server 130 streams a different screen to the TV, the Intelligent Remote will retain the same user interface or automatically adopt one of several different user interfaces, depending on which interface is required to operate that visible streamed screen on the display device 116. In each case, the Intelligent Remote may display the minimum number of buttons required to operate the active screen on the display device 116 or to navigate to a new screen available from the HHP server 130. This feature simplifies the processes of both learning how to use and operate the Patient-TV Portal. For example, many screens will only require three buttons to navigate a screen (left arrow, right arrow and enter) while other screens will require a numeric keypad (to respond to a question with a number) and still other screens will require video controls (such as pause, forward and reverse). The additional ease of use provided by the Intelligent Remote by displaying only the required buttons may be especially valuable for the older adult patient, who may have impaired eyesight and/or limited manual dexterity, and who often is confused by conventional remotes that have a large number of small buttons.

The login process described above is handled via a secure form which returns a token. The token is securely stored in a local storage (e.g., RAM 202, ROM 203, storage media 205, etc. of FIG. 2) of the user device 110. All subsequent requests to the System server are tagged with this token. When casting mode is active, the Intelligent Remote is displayed as a layer on top of the browser app of the user device 110. The browser of the user device 110 may still runs "below" the remote, out of site of the user, but the casting API is aware it is operating in casting mode and sends data to the display device 116, instructing the display device 116 to display the required Patient-TV Portal screens on the display device 116.

The Intelligent Remote may be the user's means for navigating the hearing healthcare system 100 screens on the Patient-TV Portal. For example, the patient may use the Intelligent Remote to view an educational video, answer a question about a video, select and rate one's progress on a personal hearing aid and communication goal, interact with the hearing aid troubleshooting guide of the hearing healthcare system 100, view reports on the patient's use of and inputs into the hearing healthcare system 100, set up and view appointments with the HCP, order hearing aid related supplies and equipment, and view patient reminders. Each time the patient taps on a button on a screen of the Intelligent Remote to select a Main Menu category viewed on the Patient-TV Portal screen (e.g., videos) or to select a sub-menu item viewed on the Patient-TV Portal screen (e.g., selecting a specific video such as a video on "Hearing Aid Maintenance"), the corresponding actions are activated wirelessly by signals from the Intelligent Remote to the HHP server 130. For example, the tapped action may be recorded in the reporting database, the next Patient-TV Portal screen is retrieved from the server and displayed on the TV screen, and the next Intelligent Remote screen layout is retrieved from the HHP server 130 and displayed on a screen of the user device 110.

When the patient uses the Intelligent Remote to select a video title on the Patient-TV Portal, the video content may be streamed, for example, using the HTML5 player in a browser of the HCP website and via the casting API's streaming player in casting mode. When the patient views a video on the Patient-TV Portal, the Intelligent Remote buttons may allow the patient to, for example, play, pause, rewind, and forward a video and control the presence of closed captions. The Intelligent Remote may be notified by the HHP server 130 when the video playback has been completed. At that point, the Intelligent Remote may instruct the video review quiz process (see example quiz process of FIG. 6) to begin and the Patient-TV Portal displays the first video review question. Some of the videos will have different versions for different hearing aid models or technologies. These videos will be coded to match up with the codes included in the initial input data supplied by the HCP via the HCP device 120. Also, some videos will have pause points so one or more questions or text instructions can be displayed for the patient in between video segments. If questions are provided, the Intelligent remote screen will switch from the video control buttons to the standard remote with options such as navigation arrows, an enter button and a numeric keypad that will be used to answer the questions. Once the questions are answered, the video will resume and the video controls will return to the Intelligent Remote screen.

The Intelligent Remote may be the patient's means for entering data into the hearing healthcare system 100. For example, the patient may use the Intelligent Remote to answer video review questions, answer patient daily diary questions, evaluate the patient's progress on his or her hearing aid and communication goals, make and confirm appointments with the HCP, operate the troubleshooting guide and place orders for healthcare related supplies and equipment. As the patient uses the Intelligent Remote to answer questions, the hearing healthcare system 100 collects the associated data, stores the data in the reporting database, displays the data in reports on the HCP website and the Patient-TV Portal, and downloads the data to an external database when requested to do so by the HCP.

When the patient uses the Intelligent Remote to answer a video review question on the Patient-TV Portal, the hearing healthcare system 100 retrieves the correct response from the system content database and compares it to the patient's response. The Patient-TV Portal screen, powered by the HHP server 130, either informs the patient that their response was correct or displays the correct answer for educational purposes. The patient's correct and incorrect answers to questions are sent to the reporting database where they are stored and the patient's score on each video review quiz is calculated. Such scores are posted on the HCP website and the Patient-TV portal screen.

Likewise, the Intelligent Remote may be used to control and provide inputs to the patient's Daily Diary display on the display device 116, captures the patient's responses to the patient Daily Diary questions, and sends the responses to the appropriate database in the HHP server 130. When the Intelligent Remote is notified that the final patient question of the Daily Diary has been answered, it instructs another message, such as a "tip of the day", to be retrieved from the system content database and displayed on the display device 116. After the patient reviews the additional message, the next tap of a button on the Intelligent Remote may return the patient to the Main Menu (see FIG. 4).

The patient's Daily Diary may be an interface by which a patient performs self-evaluation and tracking of their progress toward achieving one or more individualized goals. The goals tracked through the Daily Diary may include, for example, goals and related threshold values defined by the HCP and input and stored in the HHP server 130 via the HCP device 120, and user-defined goals and related thresholds defined by the patient and input and stored in the HHP server 130 via the user device 110. In some embodiments, the individualized healthcare rules may include one or more goals tracked through the patient's Daily Diary. For example, the HCP and patient may define a goal as wearing the patient wearing their hearing aid with a threshold value being a minimum number of hours a day that the patient wears their hearing aid. On a regular basis (e.g., daily), the patient may input to the Daily Diary the number of hours the hearing aid is actually worn by the patient. The HHP server 130 may store the input patient data in the databases 170 and compare the input patient data with the threshold value for the given rule. In this example, the threshold value may be a minimum of six hours per day. When the patient input indicates that the patient does not wear the hearing aid at least six hours per day, the HHP server 130 may initiate an alert with the alerting tool 156, and the alerting tool 156 may send an alert to the HCP via the HCP device 120. In some embodiments, when the patient input indicates that the patient wears the hearing aid at least six hours per day, the HHP server 130 may initiate a message with the messaging tool 157, and the messaging tool 157 may send the message to the patient via the user device 120. The message may further be displayed on the display device 116.

In addition, the patient may use the Intelligent Remote to select a set of personal hearing aid and communication goals from a list provided on the display device 116. In some embodiments, the list of personal hearing aid and communication goals may be incorporated into an educational video on selecting goals. When the video pauses, the patient may be allowed to make preliminary selections of desired goals using the Intelligent Remote. From this shorter list of goals, the patient is then asked by the hearing healthcare system 100 to select a smaller number of goals (e.g., three) as the patient's initial personal goals. Then the patient may return to the Patient-TV Portal periodically to evaluate their progress on the achievement of each goal. When each goal is achieved (e.g., a patient rating of 10 on a 10-point Likert scale), the screen on the Patient-TV Portal may automatically propose that the achieved goal be replaced by a new goal from the patient's previous "short list". The selected goals and the patient's progress evaluations are reported on the HCP website and the Patient-TV portal. Alternatively, the HCP can accommodate the patient's request to change one or more personal goals by adding and/or deleting the patient's goals on the HCP website.

The patient may use the Intelligent Remote to resolve one or more hearing aid problems. For example, the patient will navigate to the Troubleshooting menu from the Main Menu, select a problem from the list, and then interactively read instructions on the Patient-TV Portal, try out the recommended solutions, and then report the results to the HHP server 130. When the patient resolves the problem, the HHP server 130 may provide a congratulations message the patient. When the patient cannot resolve the problem, the HHP server 130 may advise the patient to contact their HCP. In both cases, the HHP server 130 will record the results in the reporting database and report the results on the HCP website.

The patient may use the Intelligent Remote to interact with the HCP in various ways. For example, from the Main Menu, the patient can select the "Contact" option and the HHP server 130 will automatically notify the HCP about the desired patient contact. In some embodiments, the HHP server 130 may post an alert on the HCP website. The result of this action may be a phone call from the HCP to the patient. Additional interactions may include the ability of the patient to order hearing aid supplies and related equipment, such as, for example, cleaning tools or batteries. The patient may use the Intelligent Remote to select and purchase a desired product, and the order will be stored in the one or more databases 170. In some embodiments, the order will appear on the HCP website. When the purchased product is shipped to the patient, a shipment notice will be provided to the user via the Patient-TV Portal. Payment can be arranged electronically using a service like PayPal or with the patient authorizing charges to his/her credit card on file at the HCP's office.

Figure 7:
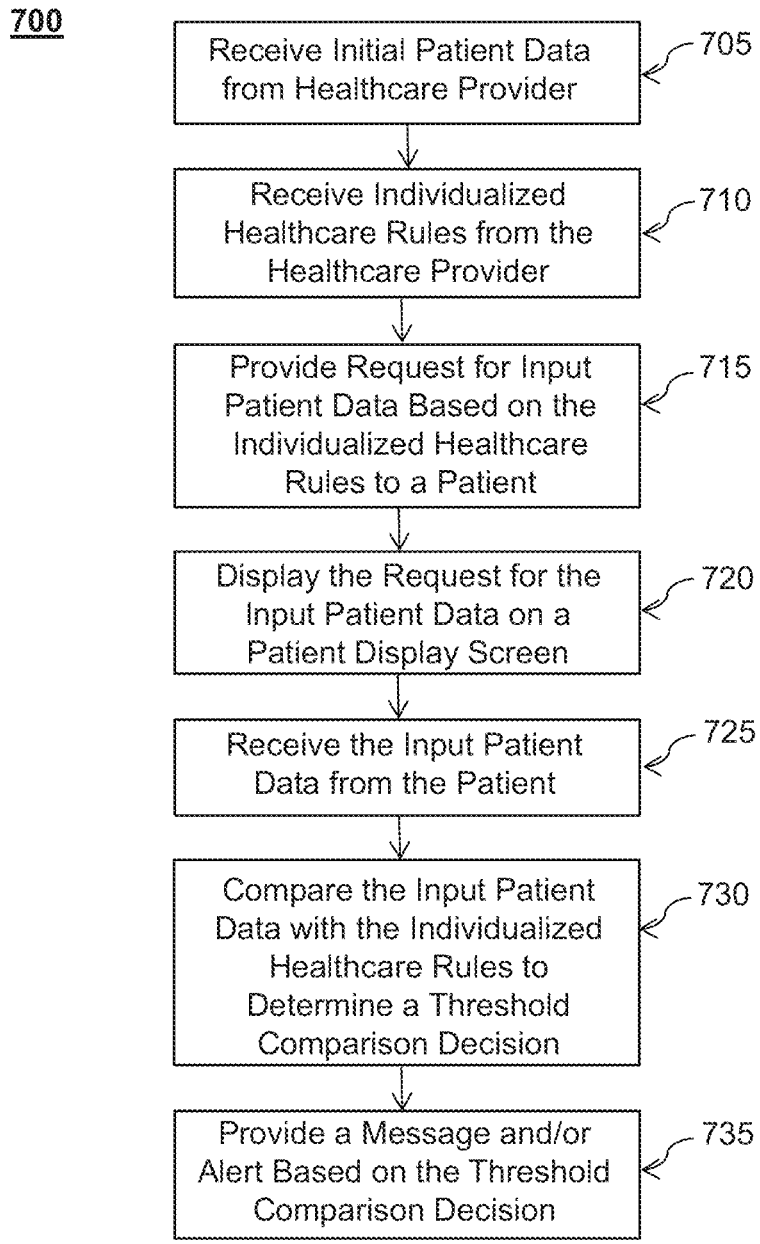
FIG. 7 is a flowchart illustrating an example method for providing education, communication, and tracking of hearing healthcare, according to certain disclosed embodiments.
Figure 8:
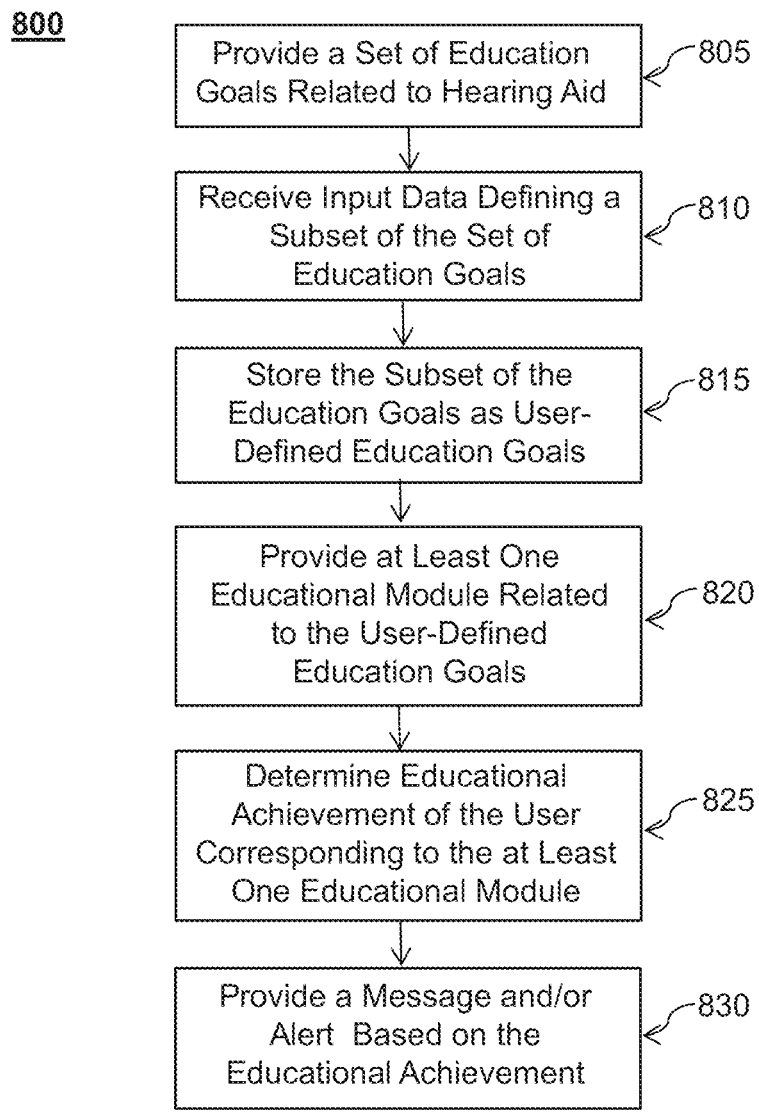
FIG. 8 is a flowchart illustrating an example method for providing education, communication, and tracking of hearing healthcare, according to certain disclosed embodiments.

FIGS. 7 and 8 are flowcharts illustrating exemplary embodiments, according to certain embodiments. In FIGS. 7 and 8, a commercially-available streaming device (e.g., CHROMECAST™) may be attached to display device 116 (e.g., a television) and synchronized with a network 190 (e.g., a secure local WiFi network). The user device 110 may be synchronized with the streaming device so that the user device 110 can be used to "cast" to the display device 116. A hearing healthcare patient may use the user device 110 to access the TELLYHEALTH™ software operating on the HHP server 130 via the network 190. The user device 110 may mirror the TELLYHEALTH™ software to the display device 116, which is on the user device 110 but not displayed on a display of the user device 110, by streaming. In addition, virtual remote control buttons may be displayed on the display of the user device 110, with the virtual remote control buttons being synchronized with the content displayed on the display device 116. The patient may use the virtual remote control buttons to navigate through the content (videos, questions, etc.) displayed on the display device 116. The patient may also use the virtual remote control buttons to respond to prompts and/or answer questions displayed on the display device 116. Data input by the patient using the virtual remote control buttons may be transmitted from the user device 110 to the HHP server 130. In some embodiments, at least a portion of the data input by the patient may be displayed on the display screen 116.

FIG. 7 is a flowchart illustrating an example method for providing education, communication, and tracking of hearing healthcare, according to certain disclosed embodiments.

At block 705, the HHP server 130 may receive initial patient data. The initial patient data may be input by an HCP via the HCP device 120. The HHP server 130 may store the input patient data in database 170 using the content management tool 153 and/or the user management tool 154. The initial patient data may include one or more value identifying an individual patient and a hearing aid used by the individual patient. For example, the initial patient data may include a patient's name, address, date of birth, hearing measures, hearing aid style and/or model information, and other information that enables the HCP to provide ongoing healthcare to a patient.

At block 710, the HHP server 130 may receive individualized healthcare rules. The individualized healthcare rules may be input by the HCP via the HCP device 120. The HHP server 130 may store the individualized healthcare rules in database 170 using the content management tool 153 and/or the user management tool 154. The HHP server 130 may generate a correspondence between the initial patient data and the individualized healthcare rules. In some embodiments, the individualized healthcare rules may be determined by the HCP, whereas in other embodiments, the individualized healthcare rules may be determined by the HCP and the patient. Each of the individualized healthcare rules may be defined specifically for the individual patient. Individualized healthcare rules may be related to one or more of hearing aid usage, hearing aid comfort, and hearing quality, and may include one or more of patient system usage rules, patient education rules, and patient experience rules. Individualized healthcare rules may include one or more threshold values, such as, for example, a hearing aid usage threshold value, a hearing aid comfort threshold value, and a hearing quality threshold value. Example individualized healthcare rules and thresholds are provided in Table 2 above.

At block 715, the HHP server 130 may provide a request for input patient data related to the individual patient based on the individualized healthcare rules. The request may be transmitted to the patient via the user device 110. At block 720, the request for input patient data may be displayed on the display device 116 for viewing by the patient and/or friends, family, or caregivers. At block 725, in response to the request, HHP server 130 may receive the input patient data from the patient, and the HHP server 130 may store the received input patient data in databases 170. The input patient data may be input by the patient to the user device 110, and transmitted to the HHP server 130 via network 190.

The request for input patient data may include one or more questions for the patient and the input patient data may include answers to the questions. In certain embodiments, the patient may be provided with an educational and experiential module (e.g., video, text, or other media) based on the individualized healthcare rules, and the request for input patient data may include requests for responses related to the content of the education video. For example, the responses may reflect a level of comprehension and understanding of the content of the educational and experiential module by the patient. In other embodiments, the request for patient input may be related to the hearing aid, and the input patient data includes responses related to one or more of hearing aid usage value reflecting an amount of time the individual patient wears the hearing aid, a hearing aid comfort threshold value reflecting a perceived comfort level of the individual patient while wearing the hearing aid, and a hearing aid quality threshold value reflecting a perceived quality level of the individual patient's hearing while wearing the hearing aid.

At block 730, for each of the individualized healthcare rules, the HHP server 130 may compare the input patient data with the individualized healthcare rule to make a threshold comparison decision. In some embodiments, comparing the input patient data with the individualized healthcare rule may include at least one of comparing the hearing aid usage value with the hearing aid usage threshold value, comparing the hearing aid comfort value with the hearing aid comfort threshold value, and comparing the hearing quality value with the hearing quality threshold value. For example, comparing the input patient data with the individualized healthcare rule may include comparing the input patient data to a threshold value of the individualized healthcare rule to determine whether the input patient data is equal to or greater than the threshold value or less than the threshold value. Then, based on the individualized healthcare rule and the corresponding threshold value, the HHP server 130 may store completion data reflecting that the patient has met or exceeded the requirements of the individualized healthcare rule, as expressed by the threshold value, or may send an alert to the HCP via the HCP device 120, indicating that the patient has not met the requirements of the individualized healthcare rule, as expressed by the threshold value.

As an example, the HHP server 130 may compare the self-reported number of hours that a patient wears their hearing aid with the minimum number of hours defined in the individualized healthcare rules. If the self-reported number of hours is equal to or greater than the minimum number of hours, the HHP server 130 may store completion data indicating that the patient has completed this requirement. In some embodiments, the HHP server 130 may also send a message to the patient, offering congratulations and encouragement to the patient on their success. The HHP server 130 may initiate the message with the messaging tool 157, and the messaging tool 157 may send a message to the patient via the user device 120. The message may further be displayed on the display device 116. If, however, the self-reported number of hours is not equal to or greater than the minimum number of hours, the HHP server 130 may the store completion data indicating that the patient has not completed this requirement, and may send an alert to the HCP, indicating that the patient has not met the requirements of the individualized healthcare rule, as expressed by the threshold value. The HHP server 130 may initiate the alert with the alerting tool 156, and the alerting tool 156 may send a message to the HCP via the HCP device 120.

At block 735, the HHP server 130 may automatically provide at least one of a message to the patient or an alert to the HCP based on the threshold comparison decision. In some embodiments, the message and/or alert may be provided to bring the individual patient into compliance with the individualized healthcare rule.

As another example, when the input patient data includes responses to a training or educational video, the HHP server 130 may evaluate the responses to determine a number of incorrect answers. If the number of incorrect answer is less than a maximum number of allowable incorrect answers, the HHP server 130 may store completion data indicating that the patient has completed this requirement. In some embodiments, the HHP server 130 may also send a message to the patient, offering congratulations and encouragement to the patient on their success. If, however, the number of incorrect answer is equal to or greater than a maximum number of allowable incorrect answers, the HHP server 130 may the store completion data indicating that the patient has not completed this requirement, and may send an alert to the HCP via the HCP device 120, indicating that the patient has not met the requirements of the individualized healthcare rule, as expressed by the threshold value.

FIG. 8 is a flowchart 800 illustrating an example method for providing education, communication, and tracking of hearing healthcare, according to certain disclosed embodiments. In particular, FIG. 8 may reflect operations occurring after the patient or other authorized user has set up their account with the HHP server 130, as discussed above.

At block 805, the HHP server 130 may provide to a user a set of education goals related to a hearing aid. The set of education goals may be provided to the user via the user device 110 and display device 116. The education goals may include patient system usage goals, patient education goals, and patient experience goals. In some embodiments, the education goals may include one or more of the individualized health care rules.

At block 810, the HHP server 130 may receive input data defining a subset of the set of the education goals. The input data may be input by the user using the user device 110, and transmitted to the HHP server 130 via network 190. For example, the user may want to improve their experience using the hearing aid, and may select specific experience goals (e.g., improved ability to hear in public places and on the telephone, etc.). At block 815, the HHP server 130 may store the selected subset of the education goals as one or more user-defined education goals. The one or more user-defined education goals may be stored in databases 170.

At block 820, the HHP server 130 may provide, to the user, at least one educational and experiential module (e.g., video, text, or other media) related to the one or more user-defined education goals. For example, if the user-defined education goals include improved ability to hear in public, the HHP server 130 may queue up an educational video that provides training and suggestions on the topic of how to hear better in a restaurant, theater, or other public location. In some embodiments, the educational and experiential module may include content review questions to evaluate the user's comprehension and understanding of the content of the educational and experiential module.

In certain embodiments, the at least one educational and experiential module includes troubleshooting information related to the hearing aid. For example, the HHP server 130 may provide, to the user, troubleshooting questions related to experiential qualities of the hearing aid, and may receive from the user, responses to the troubleshooting questions. Based on the responses to the troubleshooting questions, the HHP server 130 may determine to provide troubleshooting advice as the at least one educational and experiential module based on the responses to the troubleshooting questions. In addition, the HHP server 130 may store troubleshooting success data of the user in databases 170. The troubleshooting success data may be based on the responses to the troubleshooting questions, reflecting the user's success (or lack thereof) in troubleshooting.

At block 825, the HHP server 130 may determine educational achievement of the user. The educational achievement may correspond to the at least one educational and experiential module and may be based on the one or more user-defined education goals. In some embodiments, the HHP server 130 may determine the educational achievement of the user by providing, to the user via the user device 110, one or more review questions about the content of the at least one educational and experiential module, and receiving, from the user via the user device 110, a user response to the review question. After receiving the user response, the HHP server 130 may determine if the user response is a correct response or not, and notify the user about a result of the determining.

In certain embodiments, the HHP server 130 may determine the educational achievement of the user based on system usage data. For example, the HHP server 130 may collect user viewing data related to the at least one educational and experiential module, and compare the user viewing data to a corresponding pre-determined threshold value. Based on a comparison result, the HHP server 130 may determine whether to send the at least one of the message to the user and the alert to a hearing healthcare provider. As an example, the user viewing data may include the data of Table 1 above (e.g., cumulative number of videos viewed within a predetermined period of time, patient use/engagement with the system over time, etc.).

In other embodiments, the HHP server 130 may determine the educational achievement of the user based on user feedback about a hearing aid experience. For example, the HHP server 130 may provide, to the user via the user device 110, one or more survey questions about a hearing aid experience of the user, and may receive from the user, responses to the survey questions. The HHP server 130 may compare the survey response to corresponding pre-determined threshold values; and based on the comparison result, the HHP server 130 may determine whether to send the at least one of the message to the user and the alert to a hearing healthcare provider.

At block 830, the HHP server 130 may provide a message and/or an alert based on the educational achievement. For example, the HHP server 130 may compare the user responses to correct responses, and based on a result of the comparing, determine whether to send the at least one of the message to the user and the alert to a hearing healthcare provider. As discussed above, for example, the HHP server 130 may initiate the message with the messaging tool 157, and the messaging tool 157 may send a message to the patient via the user device 120. Additionally or alternatively, the HHP server 130 may initiate the alert with the alerting tool 156, and the alerting tool 156 may send a message to the HCP via the HCP device 120.

In some embodiments, the HHP server 130 may provide a recommended adjustment to the hearing healthcare system 100 based on the educational achievement. Recommended adjustments may include, for example, increasing a number of visits with the HCP, changing frequency or volume settings on the hearing aid, receiving redundant education via another medium (e.g., hands-on demonstrations, etc.), etc.

Additionally, the HHP server 130 may collect system usage data, which include measurements of the usage of the hearing aid system by the user and usage of at least one specific feature of the hearing aid system related to the at least one educational and experiential module. The HHP server 130 may compare the collected system usage data to a corresponding set of threshold values, and based on the comparison result, the HHP server 130 may determine whether to send the at least one of the message to the user and the alert to a hearing healthcare provider. The system usage data includes at least one of a number of times the hearing aid system is accessed by the user, a number of specific features of the hearing aid system are used by the user, and a number of specific features of the hearing aid system used within a predetermined period of time.

Further, the HHP server 130 may provide one or more reports to the user and/or the HCP. The reports may be transmitted from the HHP server 130 to the user device 110 and/or from the HHP server 130 to the HCP device 120. The one or more reports may include a summary or presentation of the user system usage data, system viewing data, etc. Based on the information included in the one or more reports, the HHP server 130 may determine a recommended adjustment to the hearing healthcare system, and may provide the recommended adjustment to HCP via an alert.

In addition, the HHP server 130 may include a cloud communications platform configured to, upon a request from the hearing healthcare education and communication system, automatically send interactive phone messages and text messages to patients and hearing healthcare providers, and receive interactive phone messages and text messages from patients and hearing healthcare providers via the hearing healthcare education and communication system to initiate survey questionnaires.

The patient may also use the Intelligent Remote to change their System password. For example, when the patient navigates to the Change Password screen from the Main Menu, the Intelligent Remote will display a QWERTY keyboard and numeric keypad that allows the patient to enter their choice of a new password. The patient can also use the Intelligent Remote to activate a video conferencing service like FaceTime via the Patient-TV Portal and communicate face-to-face with the HCP. The hearing healthcare system 100 may activate this feature using the camera built into the user device 110. This feature may be used, for example, to help resolve hearing aid problems that were not resolved by the using the Troubleshooting Guide.

When the patient has completed a session on the hearing healthcare system 100, the patient can exit the hearing healthcare system 100. For example, the user may tap the Exit button on the Intelligent Remote, or navigate to the Exit button on the Main Menu and tapping Enter.

In some embodiments, the hearing healthcare system 100 can award points for using each of its features (such as viewing an educational video or answer a patient daily diary question) and can post the point totals on the Patient-TV Portal and HCP website. These point totals may provide patients with an additional incentive to use the hearing healthcare system 100 and also enable HCPs to establish competitions among patients for motivational purposes.

In certain embodiments, the patient may give permission to a family member, friend, acquaintance, or caregiver to use the hearing healthcare system 100 to become educated on hearing aid use and care and to view patient reports on the patient TV portal. In such an embodiment, the data collected by the hearing healthcare system 100 related to hearing healthcare system 100 usage and user data entries are collected in a separate database from the patient database. In another alternative embodiment, the patient portal may be accessed by the patient on a website on a standard Internet-connected computing device.

In another embodiment, the patient can operate the hearing healthcare system 100 with a voice-activated Intelligent Remote. For example, this may be accomplished integrating an Amazon Fire Stick streaming device in conjunction with the Amazon Echo device and the Alexa voice-activated technology with the System app. In another embodiment, the patient can use a speech-to-text feature accessible by the Intelligent Remote to provide as alternative user interface for the navigation and operation of all features of the hearing healthcare system 100. In another alternative embodiment, the patient can access selected social media sites to communicate with other people with hearing loss who are using hearing aids. These communications may be achieved by presenting a QWERTY keyboard on the Intelligent Remote or using the speech-to-text interface on the Intelligent Remote that is mentioned above. In some embodiments, the Patient-TV Portal may be comprised of a standard computer, laptop, tablet or other stationary or mobile computer-based device as a website a similar user interface as shown on the Patient-TV portal that is streamed to the display device 116.

While example embodiments of the inventive concepts have been particularly shown and described, it will be understood by one of ordinary skill in the art that variations in form and detail may be made therein without departing from the spirit and scope of the invention.

What is claimed is:

1. A system for providing adaptive, integrated, and interactive hearing healthcare education and communication, comprising:
    at least one storage device storing instructions; and
    at least one computer processor configured to execute the instructions and to cause the system to perform operations comprising:
        providing, to a patient via at least one display device, at least one educational and experiential module, the at least one educational and experiential module comprising one or more of an educational module including content review questions, an experiential module including experience questions related to experiences of the patient using hearing aid, and an interactive troubleshooting module including troubleshooting questions and system responses based on patient answers;
        determining a content review score of the patient related to the content review questions, the experience questions, or the troubleshooting questions and
        determining patient viewing data corresponding to a use of both the educational module and the experiential module by the patient, wherein the patient viewing data includes at least one of a cumulative number of different videos viewed within a period of time, a title of each of the different videos viewed, and a number of times each of the different videos was viewed;
        comparing the content review score and the patient viewing data corresponding to the use of the least one educational and experiential module by the patient to threshold values to obtain a diagnostic result;
        based on the diagnostic result, automatically generating at least one of a message or an alert related to a hearing aid achievement of the patient; and
        automatically transmitting the at least one of the message or the alert to at least one of the patient and a hearing healthcare provider,
    wherein the diagnostic result is communicated to the hearing healthcare provider with the at least one of the message or the alert to assist the hearing healthcare provider in providing hearing healthcare services to the patient,
    wherein the at least one of the message or the alert provides a recommendation for at least one of improved hearing aid use or improved communication behavior of the patient based on the hearing aid achievement,
    wherein the threshold values are personalized values set for the patient by the hearing healthcare provider and stored in the at least one storage device, and
    wherein the at least one of the message or the alert is one or more of an email message, a phone call, or a text message.

2. The system of claim 1, further comprising:
    providing, to the patient via the at least one display device, at least one content review question about content of the at least one educational and experiential module;
    receiving, from the patient, patient responses to the at least one content review question;
    comparing the patient responses to correct responses;
    determining if the patient responses are the correct responses;
    determining the content review score based on a number or a percentage of the correct responses; and
    based on a result of the determining the content review score, automatically generating the at least one of the message or the alert, the at least one of the message or the alert being related to the content review score,
    wherein the patient response and the correct response are stored in the at least one storage device.

3. The system of claim 1, further comprising:
    determining the hearing aid achievement of the patient based on the diagnostic result, wherein the determining the hearing aid achievement of the patient further includes:
        providing, to the patient, a question about a hearing aid experience of the patient;
        receiving, from the patient, a patient response to the question;
        comparing the patient response to a threshold value; and
        based on a result of the comparing the patient response to the threshold value, automatically generating the at least one of the message or the alert, the at least one of the message or the alert being related to the content review score.

4. The system of claim 1, wherein the at least one computer processor is further configured to execute the instructions and to cause the system to perform operations comprising:

determining system usage data, the system usage data measuring at least one of usage of the system and usage of at least one specific feature of the system by the patient;
comparing the system usage data to one or more threshold values;
storing the system usage data and a result of the comparing the system usage data to the one or more threshold values in the at least one storage device;
based on the result of the comparing the system usage data to the one or more threshold values, automatically generating the at least one of the message or the alert the at least one of the message or the alert being related to the system usage date; and
providing at least one of one or more reports, each of the one or more reports including stored system usage data and a result of the comparing the system usage data to the one or more threshold values, and
wherein the system usage data includes at least one of: a number of times that one or more features of the system are used by the patient, and a number of specific features of the system that are used by the patient.

5. The system of claim 1, wherein the at least one educational and experiential module include troubleshooting information related to a hearing aid problem, and the at least one computer processor is further configured to execute the instructions and to cause the system to perform operations comprising:
providing, to the patient, one or more troubleshooting questions related to patient experiences using the hearing aid;
receiving, from the patient, patient responses to the one or more troubleshooting questions;
based on the patient responses to the one or more troubleshooting questions, automatically generating the at least one of the message or the alert, the at least one of the message or the alert being related to the one or more troubleshooting questions;
providing troubleshooting advice based on the patient responses to the one or more troubleshooting questions;
storing, in the at least one storage device, troubleshooting result data based on the patient responses to the one or more troubleshooting questions and a success of the patient in resolving the hearing aid problem; and
providing at least one of one or more patient reports and one or more provider reports including the stored troubleshooting result data.

6. The system of claim 1, wherein the diagnostic result relates to at least one of:
videos and/or content viewed by the patient,
a score of correct responses to the one or more content review questions,
responses to at least one questionnaire,
evaluation of progress on achieving at least one personal goal of the patient,
a result from using a troubleshooting guide, and
data transmitted to the system from the hearing aid.

7. The system of claim 1, wherein the at least one computer processor is further configured to execute the instructions and to cause the system to perform operations comprising:
providing, to the at least one display device, a set of candidate goals related to at least one of communication capabilities and performance of a hearing aid;
receiving, in response to the set of candidate goals, input data defining a subset of the set of the candidate goals; and
storing, in the at least one storage device, the subset of the set of the candidate goals as personal lifestyle goals of the patient,
wherein the at least one educational and experiential module is related to the personal lifestyle goals.

8. The system of claim 1, wherein the at least one computer processor is further configured to execute the instructions and to cause the system to perform operations comprising:
comparing the patient viewing data to a threshold value to determine the hearing aid achievement;
based on the hearing aid achievement, generating the at least one of the message or the alert, the at least one of the message or the alert being related to the hearing aid achievement; and
storing the hearing aid achievement in the at least one storage device.

9. A system for providing adaptive, integrated, and interactive hearing healthcare education and communication, comprising:
at least one storage device storing instructions; and
at least one computer processor configured to execute the instructions and to cause the system to perform operations comprising:
providing, to a patient via at least one display device, at least one educational and experiential module, the at least one educational and experiential module comprising one or more of an educational module including content review questions, an experiential module including experience questions related to experiences of the patient using hearing aid, and an interactive troubleshooting module including troubleshooting questions and system responses;
providing, to the patient via the at least one display device, at least one content review question about content of the at least one educational and experiential module;
receiving patient responses to the at least one content review question;
comparing the patient responses to correct responses;
determining if the patient responses are the correct responses;
determining a content review score of the patient related to the at least one content review question corresponding to a use of both the educational module and the experiential module by the patient and patient responses to the at least one content review question;
comparing the content review score to threshold values to obtain a diagnostic result;
based on the diagnostic result, automatically generating at least one of a message or an alert related to a hearing aid achievement of the patient;
automatically transmitting the at least one of the message or the alert to a hearing healthcare provider,
wherein the diagnostic result is communicated to the hearing healthcare provider with the at least one of the message or the alert to assist the hearing healthcare provider in providing hearing healthcare services to the patient,
wherein the at least one of the message or the alert provides a recommendation for at least one of improved hearing aid use or improved communication behavior of the patient based on the hearing aid achievement, wherein the threshold values are personalized values set for the patient by the hearing healthcare provider and stored in the at least one storage device, and wherein the at least one of the message or the alert is one or more of an email message, an automated phone call, or a text message.

10. The system of claim 9, wherein the diagnostic result also relates to at least one of:

educational content viewed by the patient, a score of correct responses to the one or more content review questions, responses to at least one experience question, evaluation of progress on achieving at least one personal goal of the patient, a result from using a troubleshooting guide, and data transmitted to the system from the hearing aid.

11. The system of claim 9, further comprising:

determining the hearing aid achievement of the patient based on the diagnostic result, including:

providing, to the patient, a hearing aid experience question about a hearing aid experience of the patient;

receiving, from the patient, a patient response to the hearing aid experience question;

comparing the patient response to a threshold value; and based on a result of the comparing of the patient response to the threshold value, automatically generating the at least one of the message or the alert.

12. The system of claim 9, wherein the at least one computer processor is further configured to execute the instructions and to cause the system to perform operations comprising:

determining system usage data, the system usage data measuring at least one of usage of the system and usage of at least one specific feature of the system by the patient;

comparing the system usage data to one or more threshold values;

storing the system usage data and a result of the comparing the system usage data to the one or more threshold values in the at least one storage device;

based on the result of the comparing the system usage data to the one or more threshold values, automatically generating the at least one of the message or the alert, the at least one of the message or the alert being related to the system usage; and providing at least one of one or more reports, each of the one or more reports including stored system usage data and a result of the comparing of the system usage data to the one or more threshold values, and wherein the system usage data includes at least one of: a number of times that one or more features of the system are used by the patient, and a number of specific features of the system that are used by the patient.

13. The system of claim 12, wherein the system usage data includes patient viewing data including at least one of a cumulative number of different videos viewed within a period of time, a title of each of the different videos viewed, and a number of times each of the different videos was viewed.

14. A system for providing adaptive, integrated, and interactive hearing healthcare education and communication, comprising:

at least one storage device storing instructions; and at least one computer processor configured to execute the instructions and to cause the system to perform operations comprising:

providing, to a patient via at least one display device, at least one educational and experiential module, the at least one educational and experiential module comprising one or more of an educational module including content review questions, an experiential module including experience questions related to experiences of the patient using hearing aid, and an interactive troubleshooting module including troubleshooting questions and system responses based on patient answers;

receiving, from the patient, patient responses to the content review questions, the experience questions, and the troubleshooting questions;

determining a content review score, an experience score, and a troubleshooting score corresponding to a use of both the educational module and the experiential module by the patient based on the patient responses to the content review questions, the experience questions and the troubleshooting questions, respectively;

comparing the at least one of the content review score, the experience score, and the troubleshooting score to threshold values to obtain at least one diagnostic result;

based on the at least one diagnostic result, automatically generating at least one of a message or an alert; and automatically transmitting the at least one of the message or the alert to a hearing healthcare provider;

wherein the at least one diagnostic result is communicated to the hearing healthcare provider with the at least one of the message or the alert to assist the hearing healthcare provider in providing hearing healthcare services to the patient, wherein the threshold values are personalized values set for the patient by the hearing healthcare provider and stored in the at least one storage device, and wherein the at least one of the message or the alert is one or more of an email message, an automated phone call, or a text message.

15. The system of claim 14, wherein the at least one of the message or the alert provides a recommendation for at least one of improved hearing aid use or improved communication behavior of the patient.

* * * * *

UNITED STATES PATENT AND TRADEMARK OFFICE
CERTIFICATE OF CORRECTION

Page 1 of 1

PATENT NO. : 11,488,492 B2
APPLICATION NO. : 17/501375
DATED : November 1, 2022
INVENTOR(S) : Alan Letzt and Stephanie Letzt It is certified that error appears in the above-identified patent and that said Letters Patent is hereby corrected as shown below:

In the Specification

At Column 1, Line 21, before the "TECHNICAL FIELD," please insert the following paragraph:
--GOVERNMENT LICENSE RIGHTS
This invention was made with government support under small business innovation research (SBIR) grant R44 AG045947 awarded by the National Institutes of Health. The government has certain rights in the invention.--

Signed and Sealed this
Twenty-seventh Day of August, 2024

Katherine Kelly Vidal
*Director of the United States Patent and Trademark Office*